(12) United States Patent
Say

(10) Patent No.: US 8,951,377 B2
(45) Date of Patent: Feb. 10, 2015

(54) MANUFACTURING ELECTROCHEMICAL SENSOR MODULE

(75) Inventor: James L. Say, Breckenridge, CO (US)

(73) Assignee: Pepex Biomedical, Inc., St. Louis, MO (US)

( * ) Notice: Subject to any disclaimer, the term of this patent is extended or adjusted under 35 U.S.C. 154(b) by 6 days.

(21) Appl. No.: 13/476,570

(22) Filed: May 21, 2012

(65) Prior Publication Data
US 2012/0291254 A1 Nov. 22, 2012

Related U.S. Application Data

(63) Continuation-in-part of application No. 13/129,333, filed as application No. PCT/US2009/064225 on Nov. 12, 2009, now Pat. No. 8,506,740.

(60) Provisional application No. 61/114,856, filed on Nov. 14, 2008, provisional application No. 61/488,015, filed on May 19, 2011.

(51) Int. Cl.
*B29C 65/00* (2006.01)
*A61B 5/15* (2006.01)
(Continued)

(52) U.S. Cl.
CPC ........... *A61B 5/1411* (2013.01); *A61B 5/14532* (2013.01); *A61B 5/14546* (2013.01); *A61B 5/1477* (2013.01); *A61B 5/150022* (2013.01); *A61B 5/150061* (2013.01); *A61B 5/150213* (2013.01); *A61B 5/150297* (2013.01); *A61B 5/150358* (2013.01); *A61B 5/150412* (2013.01); *A61B 5/150519* (2013.01); *A61B 5/150633* (2013.01); *A61B 5/150755* (2013.01); *A61B 5/15142* (2013.01); *B29C 45/14336* (2013.01); *B29L 2031/753* (2013.01); *A61B 5/1486* (2013.01); *A61B 5/157* (2013.01); *B29C 45/0062* (2013.01); *B29C 2045/0067* (2013.01); *B29C 2045/1468* (2013.01)
USPC ............ 156/250; 156/166; 156/277; 264/251

(58) Field of Classification Search
USPC ............ 156/176, 177, 178, 179, 244.19, 269, 156/303.1, 552, 166, 204, 226, 227, 245, 156/250; 264/251, 254, 255, 297.2
See application file for complete search history.

(56) References Cited

U.S. PATENT DOCUMENTS

| 1,454,224 A | 5/1923 | Schmidt |
| 2,291,720 A | 8/1942 | Hukle |

(Continued)

FOREIGN PATENT DOCUMENTS

| DE | 101 12 384 A1 | 9/2002 |
| DE | 10 2004 060 742 A1 | 7/2006 |

(Continued)

OTHER PUBLICATIONS

European Search Report for 09826755.2 mailed Oct. 5, 2012.
(Continued)

*Primary Examiner* — William Bell
(74) *Attorney, Agent, or Firm* — Merchant & Gould P.C.

(57) ABSTRACT

Certain processes for manufacturing an electrochemical sensor module include assembly first and second housing portions of sensor modules; dispensing a sensor fiber across multiple first housing portions; joining the first and second housing portions; and separating the sensor modules by cutting the sensor fiber.

14 Claims, 19 Drawing Sheets

(51) Int. Cl.
  *A61B 5/145* (2006.01)
  *A61B 5/1477* (2006.01)
  *A61B 5/151* (2006.01)
  *B29C 45/14* (2006.01)
  *B28B 5/02* (2006.01)
  *B29L 31/00* (2006.01)
  *A61B 5/1486* (2006.01)
  *A61B 5/157* (2006.01)
  *B29C 45/00* (2006.01)

(56) References Cited

U.S. PATENT DOCUMENTS

| | | | |
|---|---|---|---|
| 3,170,968 A | 2/1965 | Rokunohe et al. | |
| 3,823,035 A | 7/1974 | Sanders | |
| 3,926,201 A * | 12/1975 | Katz | 132/323 |
| 4,008,302 A * | 2/1977 | Erlichman | 264/156 |
| 4,008,717 A | 2/1977 | Kowarski | |
| 4,073,974 A | 2/1978 | Albarino et al. | |
| 4,224,125 A | 9/1980 | Nakamura et al. | |
| 4,255,487 A | 3/1981 | Sanders | |
| 4,296,533 A * | 10/1981 | Doerter | 24/581.1 |
| 4,321,057 A | 3/1982 | Buckles | |
| 4,399,099 A | 8/1983 | Buckles | |
| 4,545,382 A | 10/1985 | Higgins et al. | |
| 4,545,835 A | 10/1985 | Gusack et al. | |
| 4,552,840 A | 11/1985 | Riffer | |
| 4,573,968 A | 3/1986 | Parker | |
| 4,640,821 A | 2/1987 | Mody et al. | |
| 4,671,288 A | 6/1987 | Gough | |
| 4,704,311 A | 11/1987 | Pickering et al. | |
| 4,734,184 A | 3/1988 | Burleigh et al. | |
| 4,820,399 A | 4/1989 | Senda et al. | |
| 4,824,206 A | 4/1989 | Klainer et al. | |
| 4,846,548 A | 7/1989 | Klainer | |
| 4,880,752 A | 11/1989 | Keck et al. | |
| 4,908,115 A | 3/1990 | Morita et al. | |
| 4,919,649 A | 4/1990 | Timothy et al. | |
| 4,927,516 A | 5/1990 | Yamaguchi et al. | |
| 4,945,896 A | 8/1990 | Gade | |
| 4,974,929 A | 12/1990 | Curry | |
| 4,981,779 A | 1/1991 | Wagner | |
| 5,001,054 A | 3/1991 | Wagner | |
| 5,004,583 A | 4/1991 | Guruswamy et al. | |
| RE33,677 E | 8/1991 | Vazirani | |
| 5,047,044 A | 9/1991 | Smith et al. | |
| 5,112,455 A | 5/1992 | Cozzette et al. | |
| 5,131,138 A | 7/1992 | Crouse | |
| 5,164,229 A | 11/1992 | Hay et al. | |
| 5,165,406 A | 11/1992 | Wong | |
| 5,165,407 A | 11/1992 | Wilson et al. | |
| 5,171,689 A | 12/1992 | Kawaguri et al. | |
| 5,186,808 A | 2/1993 | Yamaguchi et al. | |
| 5,205,920 A | 4/1993 | Oyama et al. | |
| 5,217,533 A | 6/1993 | Hay et al. | |
| 5,220,920 A | 6/1993 | Gharib | |
| 5,243,982 A | 9/1993 | Möstl et al. | |
| 5,244,636 A | 9/1993 | Walt et al. | |
| 5,250,264 A | 10/1993 | Walt et al. | |
| 5,262,035 A | 11/1993 | Gregg et al. | |
| 5,264,092 A | 11/1993 | Skotheim et al. | |
| 5,264,103 A | 11/1993 | Yoshioka et al. | |
| 5,264,104 A | 11/1993 | Gregg et al. | |
| 5,264,105 A | 11/1993 | Gregg et al. | |
| 5,269,891 A | 12/1993 | Colin | |
| 5,271,815 A | 12/1993 | Wong | |
| 5,271,820 A | 12/1993 | Kinlen et al. | |
| 5,277,872 A | 1/1994 | Bankert et al. | |
| 5,298,144 A | 3/1994 | Spokane | |
| 5,298,741 A | 3/1994 | Walt et al. | |
| 5,320,725 A | 6/1994 | Gregg et al. | |
| 5,320,814 A | 6/1994 | Walt et al. | |
| 5,330,634 A | 7/1994 | Wong et al. | |
| 5,356,786 A | 10/1994 | Heller et al. | |
| 5,366,527 A | 11/1994 | Amos et al. | |
| 5,372,133 A | 12/1994 | Hogen Esch | |
| D354,347 S | 1/1995 | Knute et al. | |
| D354,559 S | 1/1995 | Knute et al. | |
| 5,384,028 A | 1/1995 | Ito | |
| 5,395,504 A * | 3/1995 | Saurer et al. | 204/403.03 |
| 5,422,246 A | 6/1995 | Koopal et al. | |
| 5,431,174 A | 7/1995 | Knute | |
| 5,437,973 A | 8/1995 | Vadgama et al. | |
| 5,478,051 A * | 12/1995 | Mauer | 264/156 |
| 5,503,728 A | 4/1996 | Kaneko et al. | |
| 5,505,828 A | 4/1996 | Wong et al. | |
| 5,512,159 A | 4/1996 | Yoshioka et al. | |
| 5,543,012 A * | 8/1996 | Watson et al. | 156/440 |
| 5,575,403 A | 11/1996 | Charlton et al. | |
| 5,593,852 A | 1/1997 | Heller et al. | |
| 5,605,152 A | 2/1997 | Slate et al. | |
| 5,609,749 A | 3/1997 | Yamauchi et al. | |
| 5,645,710 A | 7/1997 | Shieh | |
| 5,656,241 A | 8/1997 | Seifert et al. | |
| 5,720,924 A | 2/1998 | Eikmeier et al. | |
| 5,810,199 A | 9/1998 | Charlton et al. | |
| 5,849,415 A | 12/1998 | Shalaby et al. | |
| 5,863,800 A | 1/1999 | Eikmeier et al. | |
| 5,900,215 A | 5/1999 | Seifert et al. | |
| 5,951,764 A | 9/1999 | Hay et al. | |
| 5,971,941 A | 10/1999 | Simons et al. | |
| 5,972,199 A | 10/1999 | Heller et al. | |
| 5,982,959 A | 11/1999 | Hopenfeld | |
| 5,997,501 A | 12/1999 | Gross et al. | |
| 6,036,924 A | 3/2000 | Simons et al. | |
| 6,044,665 A | 4/2000 | Lysson et al. | |
| 6,048,352 A | 4/2000 | Douglas et al. | |
| D424,696 S | 5/2000 | Ray et al. | |
| D426,638 S | 6/2000 | Ray et al. | |
| 6,071,294 A | 6/2000 | Simons et al. | |
| 6,071,391 A | 6/2000 | Gotoh et al. | |
| 6,083,710 A | 7/2000 | Heller et al. | |
| 6,103,033 A * | 8/2000 | Say et al. | 156/73.1 |
| 6,103,199 A | 8/2000 | Bjornson et al. | |
| 6,107,083 A | 8/2000 | Collins et al. | |
| 6,120,676 A | 9/2000 | Heller et al. | |
| 6,143,164 A | 11/2000 | Heller et al. | |
| 6,241,863 B1 | 6/2001 | Montbouquette | |
| 6,299,757 B1 | 10/2001 | Feldman et al. | |
| 6,329,161 B1 | 12/2001 | Heller et al. | |
| 6,338,790 B1 | 1/2002 | Feldman et al. | |
| 6,379,317 B1 | 4/2002 | Kintzig et al. | |
| 6,461,496 B1 | 10/2002 | Feldman et al. | |
| 6,464,849 B1 | 10/2002 | Say et al. | |
| 6,503,381 B1 | 1/2003 | Gotoh et al. | |
| 6,560,471 B1 | 5/2003 | Heller et al. | |
| 6,561,989 B2 | 5/2003 | Whitson | |
| 6,576,101 B1 | 6/2003 | Heller et al. | |
| 6,591,125 B1 | 7/2003 | Buse et al. | |
| 6,592,745 B1 | 7/2003 | Feldman et al. | |
| 6,607,658 B1 | 8/2003 | Heller et al. | |
| 6,610,978 B2 | 8/2003 | Yin et al. | |
| 6,616,819 B1 | 9/2003 | Liamos et al. | |
| 6,618,934 B1 | 9/2003 | Feldman et al. | |
| 6,620,112 B2 | 9/2003 | Klitmose | |
| 6,676,816 B2 | 1/2004 | Mao et al. | |
| 6,706,159 B2 | 3/2004 | Moerman et al. | |
| 6,707,554 B1 | 3/2004 | Miltner et al. | |
| 6,740,214 B1 | 5/2004 | Dobson et al. | |
| 6,749,740 B2 | 6/2004 | Liamos et al. | |
| 6,783,502 B2 | 8/2004 | Orloff et al. | |
| 6,797,214 B1 * | 9/2004 | Ruuttu et al. | 264/161 |
| 6,840,912 B2 | 1/2005 | Kloepfer et al. | |
| 6,881,551 B2 | 4/2005 | Heller et al. | |
| 6,893,545 B2 | 5/2005 | Gotoh et al. | |
| 6,965,791 B1 | 11/2005 | Hitchcock et al. | |
| 7,008,799 B1 | 3/2006 | Zimmer et al. | |
| 7,058,437 B2 | 6/2006 | Buse et al. | |
| 7,211,437 B2 | 5/2007 | Schabbach et al. | |
| 7,264,139 B2 | 9/2007 | Brickwood et al. | |
| 7,282,705 B2 | 10/2007 | Brennen | |
| 7,299,081 B2 | 11/2007 | Mace et al. | |
| 7,322,942 B2 | 1/2008 | Roe | |
| 7,335,294 B2 | 2/2008 | Heller et al. | |

(56) References Cited

U.S. PATENT DOCUMENTS

| | | | |
|---|---|---|---|
| 7,344,499 | B1 | 3/2008 | Prausnitz et al. |
| 7,378,007 | B2 | 5/2008 | Moerman et al. |
| 7,396,334 | B2 | 7/2008 | Kuhr et al. |
| 7,585,278 | B2 | 9/2009 | Aceti et al. |
| 7,723,099 | B2 | 5/2010 | Miller et al. |
| 7,740,581 | B2 | 6/2010 | Buse et al. |
| 7,828,749 | B2 | 11/2010 | Douglas et al. |
| 7,829,023 | B2 | 11/2010 | Burke et al. |
| 7,860,544 | B2 | 12/2010 | Say et al. |
| 7,875,228 | B2 * | 1/2011 | Storrs et al. ............... 264/297.1 |
| 2002/0040208 | A1 | 4/2002 | Flaherty et al. |
| 2002/0098124 | A1 | 7/2002 | Bentsen et al. |
| 2003/0211619 | A1 * | 11/2003 | Olson et al. .................... 436/44 |
| 2004/0087033 | A1 | 5/2004 | Schembri |
| 2004/0102717 | A1 | 5/2004 | Qi |
| 2004/0236251 | A1 | 11/2004 | Roe et al. |
| 2005/0067737 | A1 | 3/2005 | Mills et al. |
| 2005/0089944 | A1 | 4/2005 | Shieh et al. |
| 2005/0196747 | A1 | 9/2005 | Stiene |
| 2005/0197548 | A1 | 9/2005 | Dietiker |
| 2006/0241517 | A1 | 10/2006 | Fowler et al. |
| 2007/0027385 | A1 * | 2/2007 | Brister et al. ................ 600/365 |
| 2007/0123803 | A1 * | 5/2007 | Fujiwara et al. ............. 600/583 |
| 2007/0149897 | A1 | 6/2007 | Ghesquiere et al. |
| 2007/0199818 | A1 * | 8/2007 | Petyt et al. .............. 204/403.01 |
| 2007/0218281 | A1 * | 9/2007 | Demir et al. .................. 428/389 |
| 2008/0017645 | A1 | 1/2008 | Garagiola |
| 2008/0097546 | A1 | 4/2008 | Powers et al. |
| 2008/0167578 | A1 | 7/2008 | Bryer et al. |
| 2009/0021901 | A1 | 1/2009 | Stothers |
| 2009/0032760 | A1 | 2/2009 | Muscatell |
| 2009/0069654 | A1 | 3/2009 | Yasuzawa et al. |
| 2009/0178923 | A1 | 7/2009 | Marquant et al. |
| 2009/0257917 | A1 * | 10/2009 | Nakamura et al. ........... 422/68.1 |
| 2010/0018869 | A1 | 1/2010 | Feldman et al. |
| 2010/0018871 | A1 | 1/2010 | Feldman et al. |
| 2010/0051479 | A1 | 3/2010 | Heller et al. |
| 2010/0059372 | A1 | 3/2010 | Heller et al. |
| 2010/0059373 | A1 | 3/2010 | Heller et al. |
| 2010/0072063 | A1 | 3/2010 | Heller et al. |
| 2010/0072064 | A1 | 3/2010 | Heller et al. |
| 2010/0326842 | A1 | 12/2010 | Mazza et al. |
| 2011/0000610 | A1 * | 1/2011 | Burke et al. .................. 156/269 |
| 2011/0028815 | A1 | 2/2011 | Simpson et al. |
| 2011/0086373 | A1 | 4/2011 | Wallace-Davis et al. |
| 2011/0189762 | A1 | 8/2011 | Say |
| 2011/0203941 | A1 | 8/2011 | Say |
| 2011/0265944 | A1 | 11/2011 | Say |
| 2011/0266149 | A1 | 11/2011 | Say |
| 2011/0270061 | A1 | 11/2011 | Say |

FOREIGN PATENT DOCUMENTS

| | | |
|---|---|---|
| EP | 0 256 415 A2 | 2/1988 |
| EP | 0 327 658 A1 | 8/1989 |
| EP | 0 409 033 A2 | 1/1991 |
| EP | 0 420 296 A1 | 4/1991 |
| EP | 0 592 805 A2 | 4/1994 |
| EP | 0 710 835 A2 | 5/1996 |
| EP | 0 792 620 A2 | 9/1997 |
| EP | 0 965 301 A1 | 12/1999 |
| EP | 1 462 775 | 9/2004 |
| JP | 64-3552 | 1/1989 |
| JP | 1-153952 | 6/1989 |
| JP | 1-263537 | 10/1989 |
| JP | 4-279854 | 10/1992 |
| JP | 6-174946 | 6/1994 |
| JP | 8-107890 | 4/1996 |
| JP | 2007-202632 | 8/2007 |
| WO | WO 89/07139 | 8/1989 |
| WO | WO 91/15993 | 10/1991 |
| WO | WO 94/10553 | 5/1994 |
| WO | WO 96/22730 | 8/1996 |
| WO | WO 96/39616 | 12/1996 |
| WO | WO 97/15827 | 5/1997 |
| WO | WO 00/35340 | 6/2000 |
| WO | WO 2005/051183 A1 | 6/2005 |
| WO | WO 2007/091633 A1 | 8/2007 |
| WO | WO 2008/017645 A1 | 2/2008 |
| WO | WO 2009/032760 | 3/2009 |
| WO | WO 2009/051901 | 4/2009 |
| WO | WO 2010/056869 | 5/2010 |
| WO | WO 2010/056878 | 5/2010 |
| WO | WO 2010/056878 A2 | 5/2010 |

OTHER PUBLICATIONS

Gough, D. et al., "Short-term In Vivo operation of a glucose sensor," *A.S.A.I.O. Transactions*, vol. 32, No. 1, pp. 148-150 (Jul.-Sep. 1986).

International Search Report and Written Opinion for PCT/US2008/074649 mailed Apr. 20, 2009.

International Search Report and Written Opinion for PCT/US2008/074644 mailed May 14, 2009.

International Search Report and Written Opinion for PCT/US2009/064216 mailed May 3, 2010.

International Search Report and Written Opinion for PCT/US2009/064225 mailed May 4, 2010.

International Search Report and Written Opinion for PCT/US2009/064228 mailed Jul. 1, 2010.

Jaraba, P. et al., "NADH amperometric sensor based on poly(3-methylthiophene)-coated cylindrical carbon fiber microelectrodes: application to the enzymatic determination of L-lactate," *Electrochimica Acta.*, vol. 43, No. 23, pp. 3555-3565 (1998).

Netchiporouk, L.I. et al., "Properties of carbon fibre microelectrodes as a basis for enzyme biosensors," *Analytica Chimica Acta*, vol. 303, pp. 275-283 (1995).

Sakslund, H. et al., "Development and evaluation of glucose microsensors based on electrochemical codeposition of ruthenium and glucose oxidase onto carbon fiber microelectrodes," *Journal of Electroanalytical Chemistry*, vol. 397, pp. 149-155 (1995).

Sakslund, H. et al, "Analysis of the factors determining the sensitivity of a miniaturized glucose biosensor made by codeposition of palladium and glucose oxidase onto an 8 μm carbon filter," *Journal of Electroanalytical Chemistry*, vol. 402, pp. 149-160 (1996).

\* cited by examiner

MANUFACTURING ELECTROCHEMICAL SENSOR MODULE

CROSS REFERENCE TO RELATED APPLICATIONS

This application is a continuation-in-part of application Ser. No. 13/129,333, filed Jul. 19, 2011, now U.S. Pat. No. 8,506,740, which is a 371 application of application Ser. No. PCT/US2009/064225, filed Nov. 12, 2009, which claims the benefit of provisional application Ser. No. 61/114,856, filed Nov. 14, 2008. This Application also claims the benefit of provisional application Ser. No. 61/488,015, filed May 19, 2011. The disclosures of application Ser. No. 13/129,333, provisional application Ser. No. 61/114,856, and provisional application Ser. No. 61/488,015 are incorporated herein by reference in their entirety.

TECHNICAL FIELD

The present disclosure relates to manufacturing systems and processes for producing sensors for measuring bioanalytes and, in particular, to producing sensors using continuous manufacturing systems and processes.

BACKGROUND

Electrochemical bio-sensors have been developed for detecting analyte concentrations in a given fluid sample. For example, U.S. Pat. Nos. 5,264,105; 5,356,786; 5,262,035; 5,320,725; and 6,464,849, which are hereby incorporated herein by reference in their entireties, disclose wired enzyme sensors for detecting analytes, such as lactate or glucose. Wired enzyme sensors have been widely used in blood glucose monitoring systems adapted for home use by diabetics to allow blood glucose levels to be closely monitored. Other example types of blood glucose monitoring systems are disclosed by U.S. Pat. Nos. 5,575,403; 6,379,317; and 6,893,545.

Conventional manufacturing systems and processes for producing bio-sensors involve web based conductive print technology.

SUMMARY

One aspect of the present disclosure relates to a sensor system that can be manufactured in reduced scale and that can be conveniently handled by consumers.

Another aspect of the present disclosure relates to an electrochemical sensor module for use in a sensor system that can be efficiently manufactured using a continuous manufacturing process such as a continuous insert molding process.

A further aspect of the present disclosure relates to a sensor module including a molded body that defines an analyte analysis cell and also integrates a skin piercing element, such as a lancet or canula, into the molded body.

A variety of additional aspects will be set forth in the description that follows. The aspects can relate to individual features and to combinations of features. It is to be understood that both the forgoing general description and the following detailed description are exemplary and explanatory only and are not restrictive of the broad concepts upon which the embodiments disclosed herein are based.

DETAILED DESCRIPTION

Figure 1:
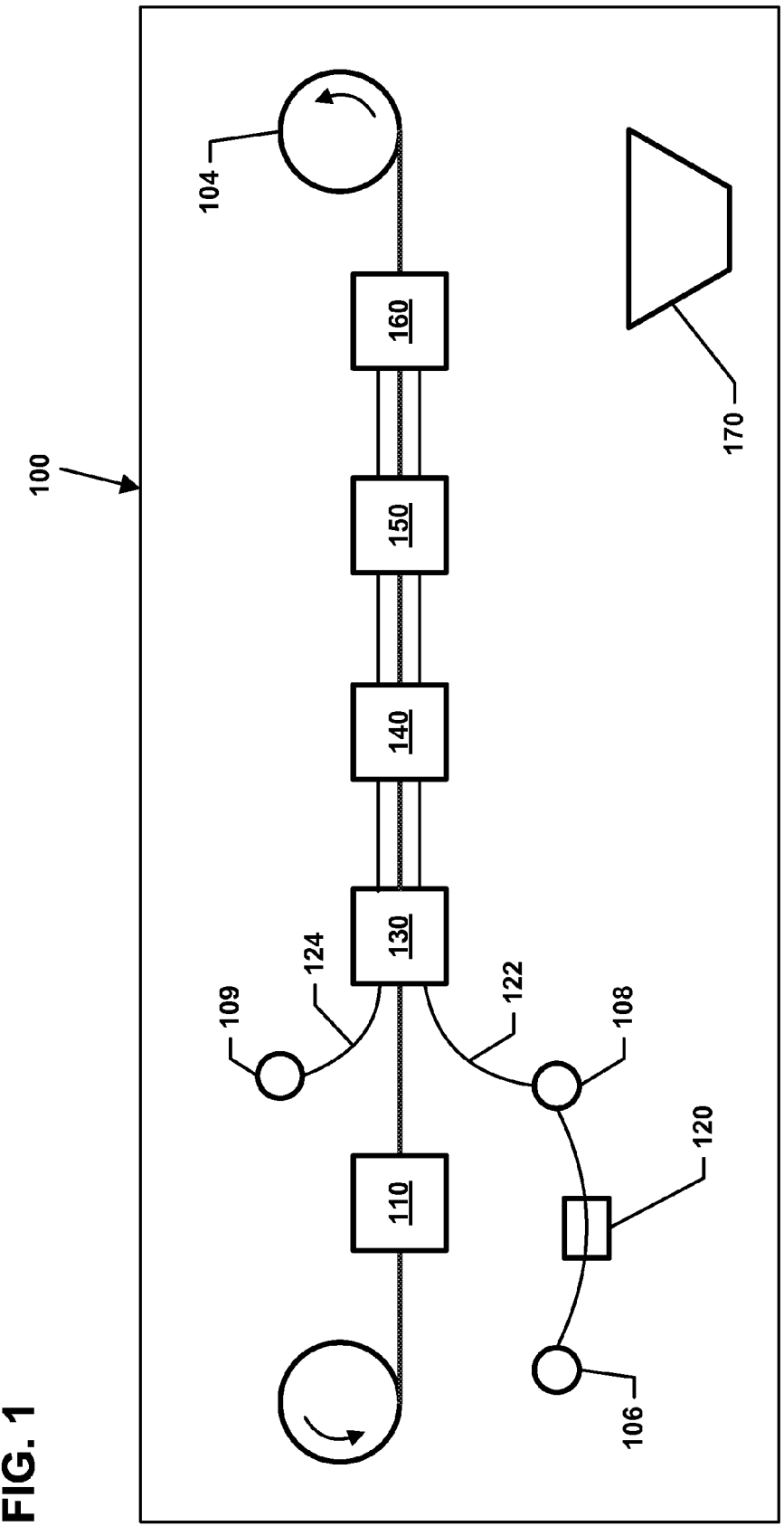
FIG. 1 is a schematic block diagram of a manufacturing system configured to produce sensor modules in accordance with the principles of the present disclosure.

Reference will now be made in detail to exemplary aspects of the present disclosure which are illustrated in the accompanying drawings. Wherever possible, the same reference numbers will be used throughout the drawings to refer to the same or like parts.

The following definitions are provided for terms used herein:

A "working electrode" is an electrode at which the analyte (or a second compound whose level depends on the level of the analyte) is electrooxidized or electroreduced with or without the agency of an electron transfer agent.

A "reference electrode" is an electrode used in measuring the potential of the working electrode. The reference electrode should have a generally constant electrochemical potential as long as no current flows through it. As used herein, the term "reference electrode" includes pseudo-reference electrodes. In the context of the disclosure, the term "reference electrode" can include reference electrodes which also function as counter electrodes (i.e., a counter/reference electrode).

A "counter electrode" refers to an electrode paired with a working electrode to form an electrochemical cell. In use, electrical current passes through the working and counter electrodes. The electrical current passing through the counter electrode is equal in magnitude and opposite in sign to the current passing through the working electrode. In the context of the disclosure, the term "counter electrode" can include counter electrodes which also function as reference electrodes (i.e., a counter/reference electrode).

A "counter/reference electrode" is an electrode that functions as both a counter electrode and a reference electrode.

An "electrochemical sensing system" is a system configured to detect the presence and/or measure the level of an analyte in a sample via electrochemical oxidation and reduction reactions on the sensor. These reactions are converted (e.g., transduced) to an electrical signal that can be correlated to an amount, concentration, or level of an analyte in the sample. Further details about electrochemical sensing systems, working electrodes, counter electrodes and reference electrodes can be found at U.S. Pat. No. 6,560,471, the disclosure of which is hereby incorporated herein by reference in its entirety.

"Electrolysis" is the electrooxidation or electroreduction of a compound either directly at an electrode or via one or more electron transfer agents.

An "electron transfer agent" is a compound that carries electrons between the analyte and the working electrode either directly or in cooperation with other electron transfer agents. One example of an electron transfer agent is a redox mediator.

A "sensing layer" is a component of the sensor which includes constituents that facilitate the electrolysis of the analyte. The sensing layer may include constituents such as an electron transfer agent, a catalyst which catalyzes a reaction of the analyte to produce a response at the electrode, or both.

The present disclosure is directed to a manufacturing system configured to produce one or more sensor modules configured for analyte monitoring (e.g., glucose single-point monitoring, lactate single-point monitoring, etc.). Each sensor module includes a housing containing an analysis cell configured to hold a fluid sample, at least two elongated electrodes arranged to enter the analysis cell, and contacts for electrically connecting the electrodes to external connectors. In a preferred embodiment, the elongated electrodes include a continuously coated working electrode and an uncoated reference electrode. In one embodiment, one or more of the elongated electrodes includes a composite conductive monofilament (CCM) electrode. In other embodiments, the housing can contain additional electrodes having differing enzyme coatings. The analysis cell can be configured for coulormetric or amperometric assays.

In general, each sensor module is produced by a continuous manufacturing system, which includes a manufacture and assembly line in which a preformed carrier travels to different stations along a direction of travel. Components of the sensor modules are formed and/or assembled together at different stations as the carrier progresses through the line. In a preferred embodiment, each sensor module is produced by a "reel to reel" manufacturing system in which the carrier extends between first and second reels. The continuous manufacturing system is particularly suitable for producing very small parts in production quantities of tens of millions of units per year per system.

FIG. 1 is a schematic block diagram of one example continuous manufacturing system 100 configured to produce a sensor module in accordance with the principles of the present disclosure. The manufacturing system 100 includes a carrier 101 extending between a first carrier reel 102 and a second carrier reel 104. The carrier 101 travels along a direction of travel D1 from the first carrier reel 102 to the second carrier reel 104 when indexed by one or both carrier wheels 102, 104. In one embodiment, the carrier 101 is formed from metal. In another embodiment, the carrier 101 is formed from a polymer composition. In other embodiments, however, the carrier 101 can be preformed from any suitable material.

The manufacturing system 100 also includes a molding station 110, an electrode insertion station 130, a folding station 140, a joining station 150, a stamping station 160, and a collection station 170. The carrier 101 passes by each of these stations 110, 130, 140, 150, 160, 170 as the carrier 101 is indexed between the first and second carrier reels 102, 104. Support components of the sensor module are formed at the molding station 110. In general, the molding station 110 overmolds one or more components of each sensor module onto the carrier 101. In a preferred embodiment, the molding station 110 includes an in-line injection molding machine. In various other embodiments, however, different types of molding machines can be used.

Electrodes for use in the sensor modules are created by coating sensor chemistry onto an elongated member (e.g., a composite monofilament) at a coating station 120. In a preferred embodiment, the coating station 120 includes at least two filament reels 106, 108 containing a wound elongated member. Typically, the elongated member includes a continuously conductive elongated member. In one embodiment, the elongated member is a composite monofilament. The elongated member is fed from the first reel 106 to the second reel 108 to continuously coat the elongated member with a layer of sensor chemistry, such as silver chloride, to form a working electrode 122. Accordingly, the second reel 108 contains a wound working electrode 122 when the coating stage is complete. At least a third filament reel 109 contains a wound, uncoated elongated member for forming another electrode 124 (e.g., a reference electrode, a counter electrode, or a reference/counter electrode).

The elongated member to be coated can include a thread, a carbon fiber, a metal wire, or another such elongated member. Preferably, at least a portion of the elongated member is electrically conductive. In certain embodiments, each elongated member can have a composite structure and can include a fiber having a dielectric core surrounded by a conductive layer suitable for forming an electrode. A preferred composite fiber is sold under the name Resistat® by Shakespeare Conductive Fibers LLC. This composite fiber includes a composite nylon, monofilament, conductive thread material made conductive by the suffusion of about a 1 micron layer of carbonized nylon isomer onto a dielectric nylon core material. The Resistat® material is comprised of isomers of nylon to create the basic 2 layer composite thread. However, many other polymers are available for the construction, such as: polyethylene terephthalate, nylon 6, nylon 6,6, cellulose, polypropylene cellulose acetate, polyacrylonitrile and copolymers of polyacrylonitrile for a first component and polymers such as of polyethylene terephthalate, nylon 6, nylon 6,6, cellulose, polypropylene cellulose acetate, polyacrylonitrile and copolymers of polyacrylonitrile as constituents of a second component. Inherently conductive polymers (ICP) such as doped polyanaline or polypyrolle can be incorporated into the conductive layer along with the carbon to complete the formulation. In certain embodiments, the ICP can be used as the electrode surface alone or in conjunction with carbon. The Resistat® fiber is availability in diameters of 0.0025 to 0.016 inches, which as suitable for sensor electrodes configured in accordance with the principles of the present disclosure. Example patents disclosing composite fibers suitable for use in practicing sensor modules configured in accordance with the principles of the present disclosure include U.S. Pat. Nos. 3,823,035; 4,255,487; 4,545,835 and 4,704,311, which are hereby incorporated herein by reference in their entireties.

The sensing layers provided at working electrodes 122 of sensor modules configured in accordance with the principles of the present disclosure can include a sensing chemistry, such as a redox compound or mediator. The term redox compound is used herein to mean a compound that can be oxidized or reduced. Example redox compounds include transition metal complexes with organic ligands. Preferred redox compounds/mediators include osmium transition metal complexes with one or more ligands having a nitrogen containing heterocycle such as 2,2'-bipyridine. The sensing material also can include a redox enzyme. A redox enzyme is an enzyme that catalyzes an oxidation or reduction of an analyte. For example, a glucose oxidase or glucose dehydrogenase can be used when the analyte is glucose. Also, a lactate oxidase or lactate dehydrogenase fills this role when the analyte is lactate. In sensor systems, such as the one being described, these enzymes catalyze the electrolysis of an analyte by transferring electrons between the analyte and the electrode via the redox compound. Further information regarding sensing chemistry can be found at U.S. Pat. Nos. 5,264,105; 5,356,786; 5,262,035; and 5,320,725, which were previously incorporated by reference in their entireties.

The electrodes (e.g., working electrode and reference electrode) 122, 124 are mounted to the molded components of the sensor module at the insertion station 130. In general, the second reel 108 containing the working electrode and the third reel 109 containing the reference electrode (i.e., or counter electrode or reference/counter electrode) 124 are arranged to feed the electrodes 122, 124 into the insertion station 130, which aligns the electrodes 122, 124 with the molded sensor module components. Typically, the insertion station 130 aligns the elongated members forming the electrodes 122, 124 with the components on the carrier 101 without cutting the elongated members. In other embodiment, additional reels holding wound reference electrodes, counter electrodes, and/or counter/reference electrodes also can be positioned relative to the insertion station 130 to feed the electrodes onto the components without cutting the electrodes. This continuous insertion station 130 allows low cost, high volume production of CCM-type sensor modules at significantly smaller sizes, improved repeatability, and with less process waste than conventional systems and methods.

The folding station 140 arranges the sensor module components into a final configuration in which the components are aligned. In one embodiment, the folding station 140 is configured to bend the carrier 101 to align two sides of the carrier 101. In another embodiment, the folding station 140 is configured to break the carrier along a fold axis to align two sides of the carrier 101. The joining station 150 secures (e.g., presses, welds, molds, heat seals, etc.) the components together to form the sensor module. In one embodiment, the joining station 150 includes a laser welder. In another embodiment, the joining station 150 includes an overmold machine.

The separation station 160 separates the sensor modules from the carrier 101 to produce completed sensor modules. In one embodiment, the separation station 160 includes a stamping machine. In another embodiment, the separation station 160 includes a laser cutting machine. Other types of separation devices also can be used within the scope of the disclosure. The completed sensor modules are accumulated at the collection station 170 after being removed from the carrier 101. The remainder of the carrier 101 is wound onto the second carrier wheel 104.

Figure 2:
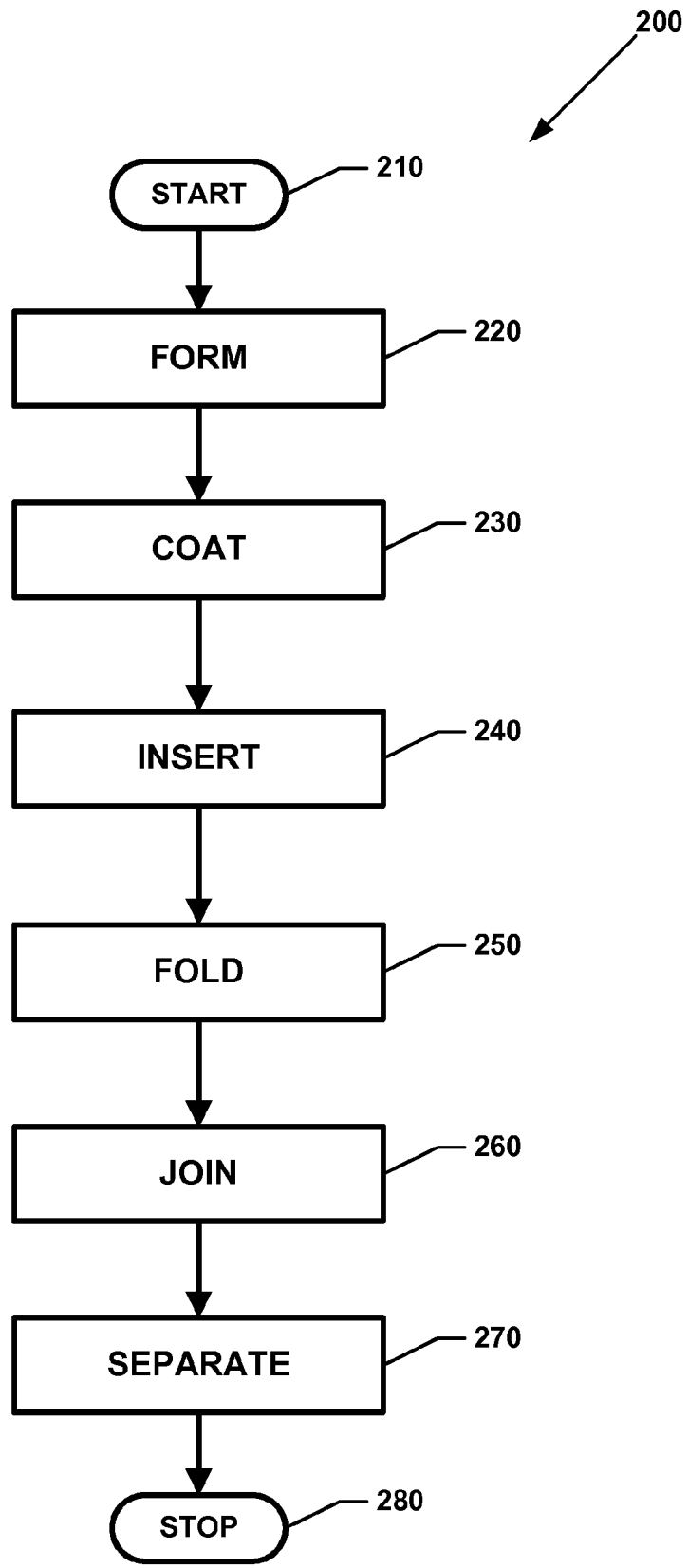
FIG. 2 is a flowchart illustrating an operation flow for an example manufacturing process by which one or more sensor modules can be produced, e.g., using the manufacturing system of FIG. 1.

FIG. 2 is a flowchart illustrating an operation flow for an example manufacturing process 200 by which one or more sensor modules can be produced using the manufacturing system 100 of FIG. 1. Of course, other systems can implement the steps of manufacturing process 200 in accordance with the principles of the present disclosure. The manufacturing process 200 begins at a start module 210, performs any appropriate initialization procedures, and proceeds to a form operation 220.

Figure 4:
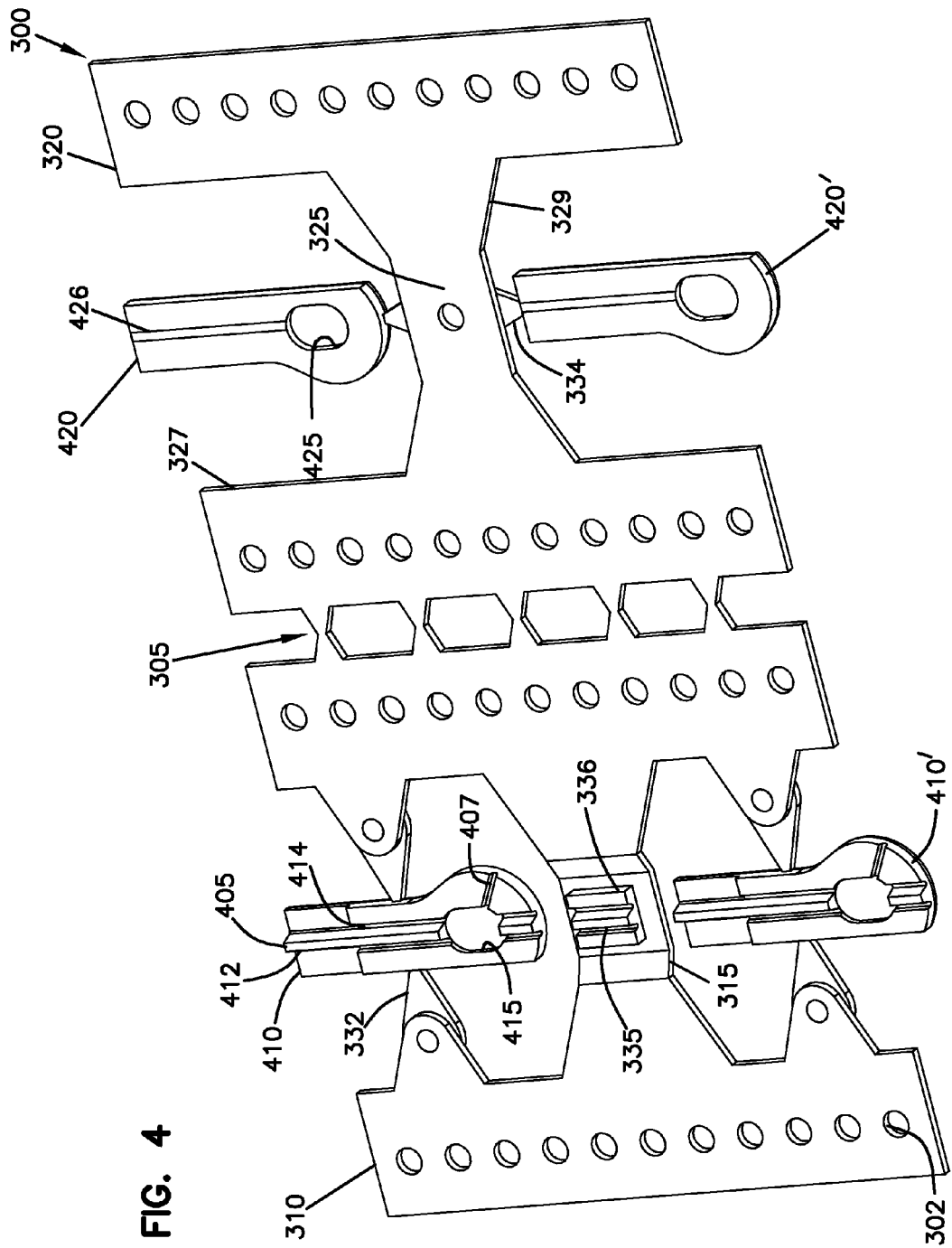
FIG. 4 is a top, perspective view of the portion of the carrier of FIG. 3 after sensor module components have been molded onto the body of the carrier in accordance with the principles of the present disclosure.

The form operation 220 produces one or more components of the sensor module onto the carrier 101 (see FIG. 4). For example, the form operation 220 can mold a housing of the sensor module onto the carrier 101. In some embodiments, the form operation 220 produces the housing in a "clamshell" configuration having at least two opposing portions. For example, in form operation 220, the carrier 101 can enter an in-line injection molding machine 110, which simultaneously molds both portions of the housing on the carrier 101 (see FIG. 1). In a preferred embodiment, the two opposing portions are half portions. In other embodiments, however, the opposing portions can be unequal in size and/or shape.

A coat operation 230 adds sensor chemistry to at least one elongated member, such as a monofilament, to produce a first electrode (e.g., a working electrode). In a preferred embodiment, the coat operation 230 continuously coats sensor chemistry on the elongated member at a reel-to-reel coating station. For example, in one embodiment, the elongated member can unwind from a first filament reel, such as reel 106 of FIG. 1, pass through the sensor chemistry, and wind up onto a second filament reel, such as reel 108 of FIG. 1, during the coat operation 230. In one embodiment, the sensor chemistry is continuously coated onto the elongated member. The coated elongated member is referred to as a working electrode.

An insert operation 240 adds the working electrode and a second electrode (e.g., a reference electrode, a counter electrode, or a reference/counter electrode) to the molded components arranged on the carrier 101. Additional electrodes may be added to the molded components in certain embodiments of the sensor modules. The insert operation 240 can feed the electrodes 122, 124 of FIG. 1 from the reels 108, 109, respectively, into the insertion station 130 at which the insert operation 240 can route the electrodes into channels defined in the molded components. The insert operation 240 arranges each electrode to align with a contact element configured to route any signals generated at the electrode out of the sensor module housing.

A fold operation 250 arranges the components and electrodes of each sensor module into a final configuration. For example, the fold operation 250 can align and press together two portions of a sensor module housing to form an enclosure around the coated and uncoated electrodes. A join operation 260 seals together the components of the sensor module. For example, the join operation 260 can weld, glue, melt, fasten, or otherwise secure the components together to form a completed sensor modules. A separate operation 270 removes (e.g., mechanically cuts, stamps, cuts with a laser, etc.) the completed sensor modules from the carrier 101 (FIG. 1). The manufacturing process 200 completes and ends at a stop module 280.

Figure 3:
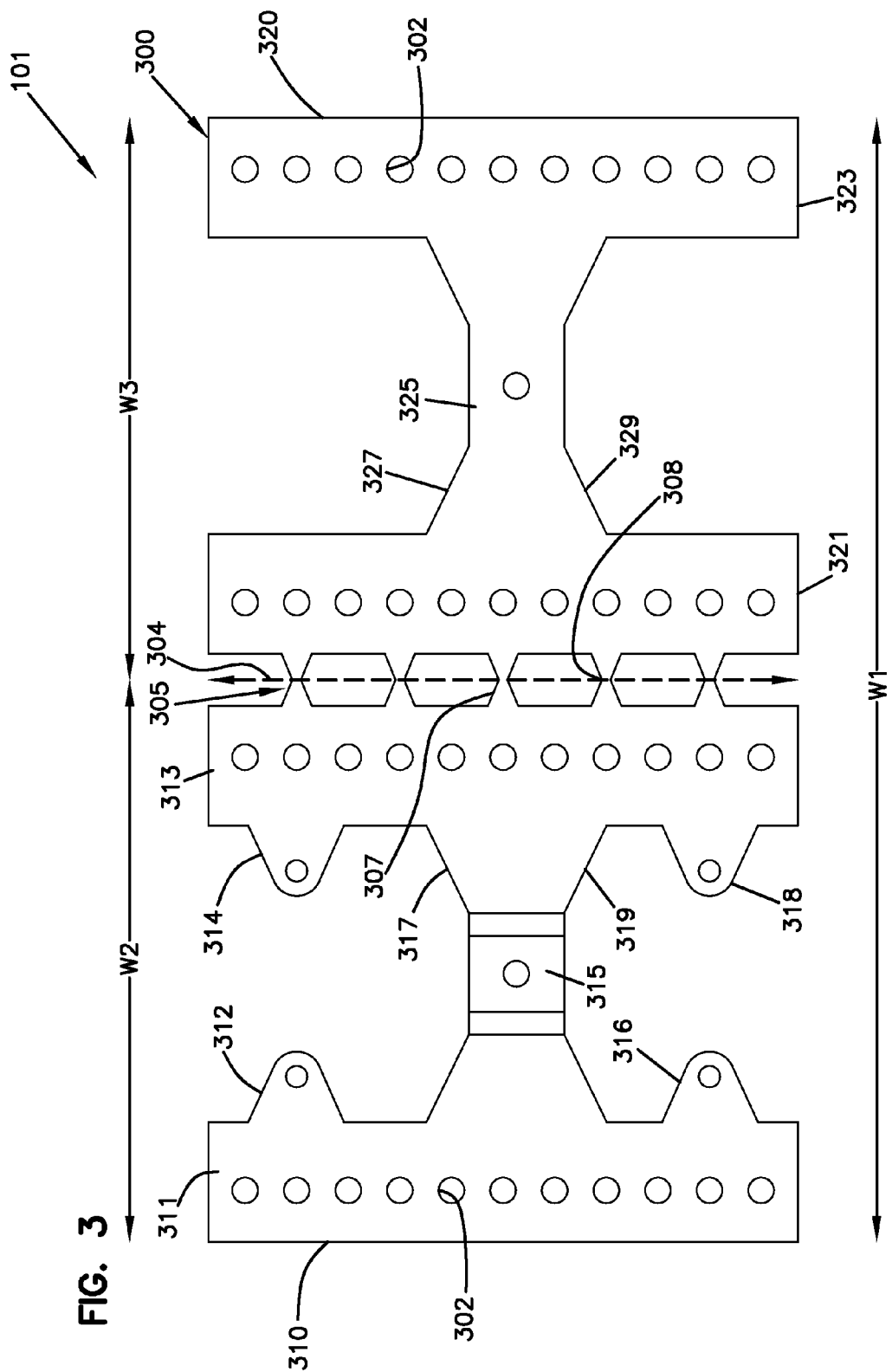
FIG. 3 is a planar view of a portion of an example carrier that can be indexed through the processing stations of the manufacturing system of FIG. 1 in accordance with the principles of the present disclosure.

The principles of the application can be further understood by walking through an example application in which a generic sensor module is manufactured. FIG. 3 shows a portion of one example carrier 101 that can be indexed through the different processing stations 110, 120, 130, 140, 150, 160 of the manufacturing system 100 of FIG. 1. The carrier 101 includes a generally flat carrier body 300 defining at least one series of index holes 302 configured to receive index pins to advance the carrier through the system 100. In the example shown, the carrier body 300 defines four series of index holes 302. In other embodiments, however, the carrier body 300 can define greater or fewer series of index holes 302.

The carrier body 300 defines a profile that is configured to support the components of the sensor module. In a preferred embodiment, the carrier body 300 is produced by roll stamping a high-precision profile on a stainless steel or suitable polymer tape and storing the prepared tape on a collector reel, such as the first carrier reel 102. One or more components can be molded to the carrier body 300 as the carrier 101 is indexed. In certain embodiments, multiple components of one sensor module can be molded across the width W1 of the carrier body 300.

The carrier body 300 includes a fold feature 305 that splits the carrier body 300 into a first section 310 and a second section 320 along a fold axis 304. The first section 310 has a width W2 and the second section 320 has a width W3. In a preferred embodiment, the fold feature 305 of the carrier body 300 is a midline fold feature that splits the carrier body 300 along a central axis into two halves (i.e., so that the widths W2, W3 of the first and second sections are about equal). In other embodiments, however, the fold feature 305 can split the carrier body 300 into sections 310, 320 of different sizes.

In general, the fold feature 305 is a weakened or reduced portion of the carrier body 300 at which the carrier body 300 is configured to bend and/or break. In the example shown, the fold feature 305 includes multiple connecting members 307 extending between the first and second sections 310, 320. The connecting members 307 have a tapered center 308 that is configured to bend to enable the carrier body 300 to be folded at the fold feature 305.

Folding the carrier body 300 along the fold axis 304 aligns the first section 310 with the second section 320. Accordingly, the fold feature 305 of the carrier body 300 enables opposing portions of sensor components to be molded onto the first and second sections 310, 320 of the carrier body 300 and subsequently assembled together by folding the carrier body 300 along the fold axis 304. For example, the fold feature 305 enables different housing portions to be molded face-up on opposite sides of the carrier body 300. Additional features can be added to the interior of the sensor module after the support components are molded on the carrier body 300 and prior to folding the carrier body 300.

The carrier body 300 shown in FIG. 3 has a profile configured to support at least two molded components of a sensor module. Each section 310, 320 includes a first support wall 311, 321 and a second support wall 313, 323 connected by a third support wall 315, 325, respectively, to form an "H" shape. The support walls 311, 313, 315 of the first section 310 define first and second gaps 317, 319 within which components of the sensor modules can be molded. The support walls 321, 323, 325 of the second section 320 define first and second gaps 327, 329 within which opposing components of the sensor modules can be molded.

First and second support members 312, 314 protrude into the first gap 317 in the first section 310 from the side walls 311, 313, respectively. Third and fourth support members 316, 318 protrude into the second gap 319 in the first section 310 from the side walls 311, 313, respectively. The support members 312, 314, 316, 318 are configured to provide support for molded components of the sensor module. For example, in FIG. 3, each support member 312, 314, 316, 318 defines an opening at an end opposite the support walls 311, 313 to which a component can be molded. In the example shown, the third support walls 315, 325 of the two sections 310, 320 also define openings to which components or support members can be molded.

FIG. 4 shows the portion of the carrier 101 of FIG. 3 after sensor module components have been molded onto the body 300 of the carrier 101 (e.g., at the mold station 110 of FIG. 1). In the example shown, components of two different sensor modules have been molded onto the visible portion of the carrier body 300. Components of a first sensor module 400 have been molded into the first gaps 317, 327 of the first and second sections 310, 320 and components of a second sensor module 400' have been molded into the second gaps 319, 329 of the first and second sections 310, 320.

The first sensor module 400 (FIG. 6) includes a first housing portion 410 molded at the first gap 317 of the first section 310 and a second housing portion 420 molded at the first gap 327 of the second section 320. The first housing portion 410 is formed to be generally complementary to the second housing portion 420. Each of the housing portions 410, 420 defines a depression 415, 425, respectively. When the housing portions 410, 420 are assembled, the depressions 415, 425 align to form an analysis cell within the sensor module 400. In a some embodiment, each depression 415, 425 is about 0.01 inches (0.25 millimeters) to about 0.05 inches (1.27 millimeters) across at a largest dimension and about 0.002 (0.05 millimeters) to about 0.005 inches (0.13 millimeters) deep. In a preferred embodiment, each depression 415, 425 is about 0.03 inches (0.76 millimeters) across at the largest dimension and about 0.003 (0.08 millimeters) deep.

At least one of the housing portions 410, 420 defines a groove 407 to form a sample path between the analysis cell and the exterior of the sensor module 400. In the example shown, the groove 407 is defined in the first housing portion 410. In another embodiment, both housing portions 410, 420 can define channels that align to form the groove 407. Channels configured to hold continuous electrodes also are defined in at least one of the housing portions 410, 420. In the example shown, electrode channels 412, 414 are defined in the first housing portion 410. In the example shown, the electrode channels 412, 414 extend from one end of the housing portion 410, through the analysis cell, to an opposite end of the housing portion 410. In one embodiment, the electrode channels 412, 414 are V-shaped channels. In other embodiments, however, the channels 412, 414 can have any suitable shape (e.g., U-shaped, squared, etc.). In certain embodiments, corresponding electrode channels can be defined in the second housing portion 420.

In some embodiments, one or both housing portions 410, 420 also can include attachment members configured to secure the housing portions 410, 420 together. For example, one of the housing portions 410, 420 can include pegs or other protrusions configured to mate with openings, depressions, or grooves defined in the other of the housing portions 410, 420. In one embodiment, the first housing portion 410 defines an extended protrusion 405 that is configured to fit within a corresponding channel 426 defined in the second housing portion 420 (e.g., see FIG. 8). In another embodiment, the extended protrusion 405 provides an anchor which can be embedded within a molded or welded section joining the two housing portions 410, 420.

Support members also can be molded onto the carrier body 300 to couple the sensor module components to the carrier body 300 and/or to align the sensor module components on the carrier body 300. In FIG. 4, a first set of connecting support members 332 extend between the support members 312, 314 of the carrier body 300 and the first housing portion 410 to secure the first housing portion 410 to the carrier body 300. A second set of connecting support members 334 extend between the third support member 325 and the second housing portion 420 410 to secure the second housing portion 420 to the carrier body 300. In one embodiment, the connecting support members 334 are integrally formed (see FIG. 6). In other embodiments, the first housing portion 410 can be secured to the third support member 315 of the first section and/or the second housing portion 420 can be secured to support members extending from the walls 321, 323 of the second section 320.

In the example shown, an alignment member 336 is arranged on the third support member 315 of the first section 310. The alignment member 336 defines grooves 335 configured to hold continuous filaments that will form electrodes of the sensor modules. The alignment member 336 has generally the same number of grooves 335 as the first housing portion 410 has electrode channels 412, 414. In FIG. 4, the alignment member 336 defines two grooves 335. The grooves 335 of the alignment member 336 co-axially align with the electrode channels 412, 414 of the first housing portion 410.

Figure 5:
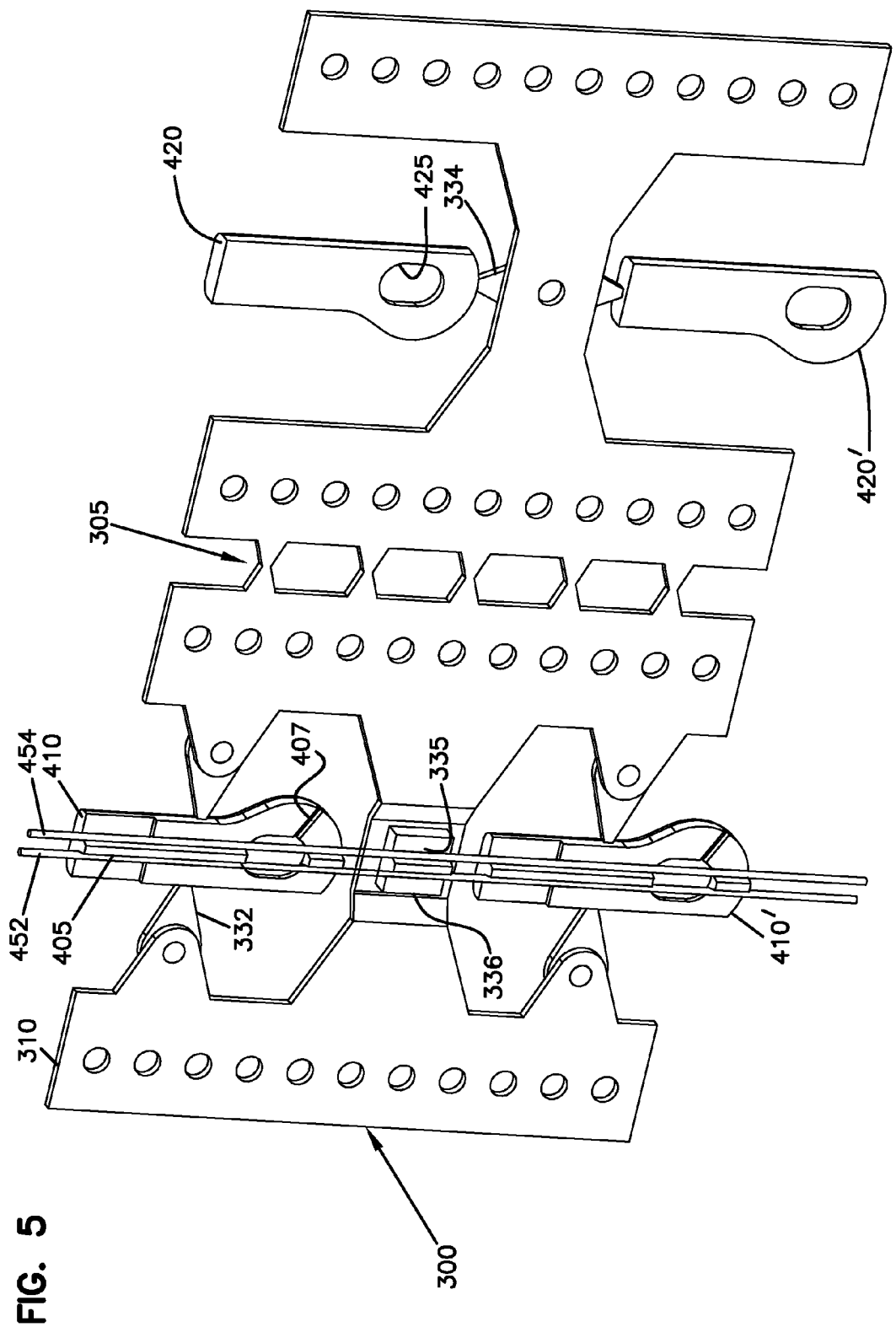
FIG. 5 is a perspective view of the portion of the carrier of FIG. 4 after a first electrode and a second electrode have been routed onto the molded sensor components in accordance with the principles of the present disclosure.

FIG. 5 shows the portion of the carrier 101 of FIG. 3 after a first electrode 452 and a second electrode 454 have been routed onto the molded sensor components (e.g., at the insertion station 130 of FIG. 1). In the example shown, the electrodes 452, 454 are routed on either side of the extended protrusion 405. The first electrode 452 is routed into the first electrode channel 412 and the second electrode 454 is routed into the second electrode channel 414. Accordingly, the electrodes 452, 454 pass through the depression 415 partially forming the analysis cell. Typically, the first electrode 452 is a working electrode formed by coating sensor chemistry onto an elongated member and the second electrode 454 is a reference electrode formed from an uncoated elongated member.

In the example shown, the electrodes 452, 454 extend longitudinally along the first section 310 of the carrier body 300 in continuous strands. Accordingly, the electrodes 452, 454 extend from the first housing portion 410 of the first sensor module 400 to the first housing portion 410' of the second sensor module 400'. The alignment member 336 aids in guiding the electrodes 452, 454 into position on the sensor modules 400, 400'. For example, each electrode 452, 454 can be arranged within a groove 335 of the alignment member 336.

In the example shown, the third support wall 315 of the first section 310 has a depressed or "stepped out" portion to accommodate the alignment member 336 and the electrodes 452, 454. The depressed portion forms a channel 308 (FIG. 6) when the second section 310 of the carrier body 300 is folded over the first section 310. The electrodes 452, 454 are routed through the channel 308 when passing between components of the sensor modules 400, 400'.

Figure 6:
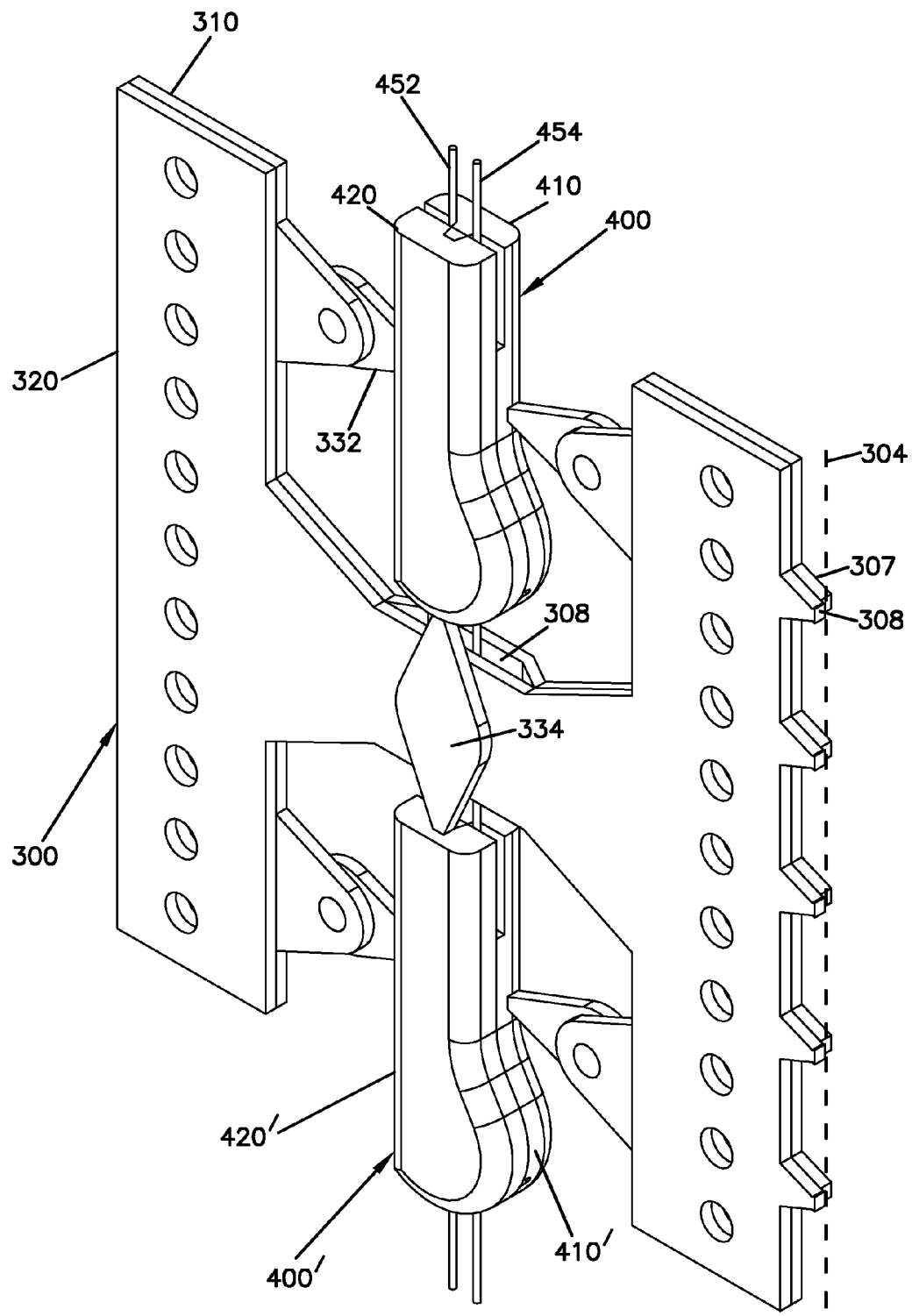
FIG. 6 is a perspective view of the portion of the carrier of FIG. 5 after the carrier has been rolled or folded along a fold axis to align the first and second sections of the carrier body in accordance with the principles of the present disclosure.

FIG. 6 shows the portion of the carrier 101 of FIG. 3 after the carrier 101 has been rolled or folded along the fold axis 304 (FIG. 3) to align the first and second sections 310, 320 of the carrier body 300 (e.g., at fold station 140 of FIG. 1). In one embodiment, the connecting members 307 extending between the first and second sections 310, 320 of the carrier body 300 are broken at their tapered centers 308 along the fold axis 304 as shown in FIG. 6. In other embodiments, however, the connecting members 307 bend sufficiently to enable the first section 310 to align with the second section 320.

Figure 9:
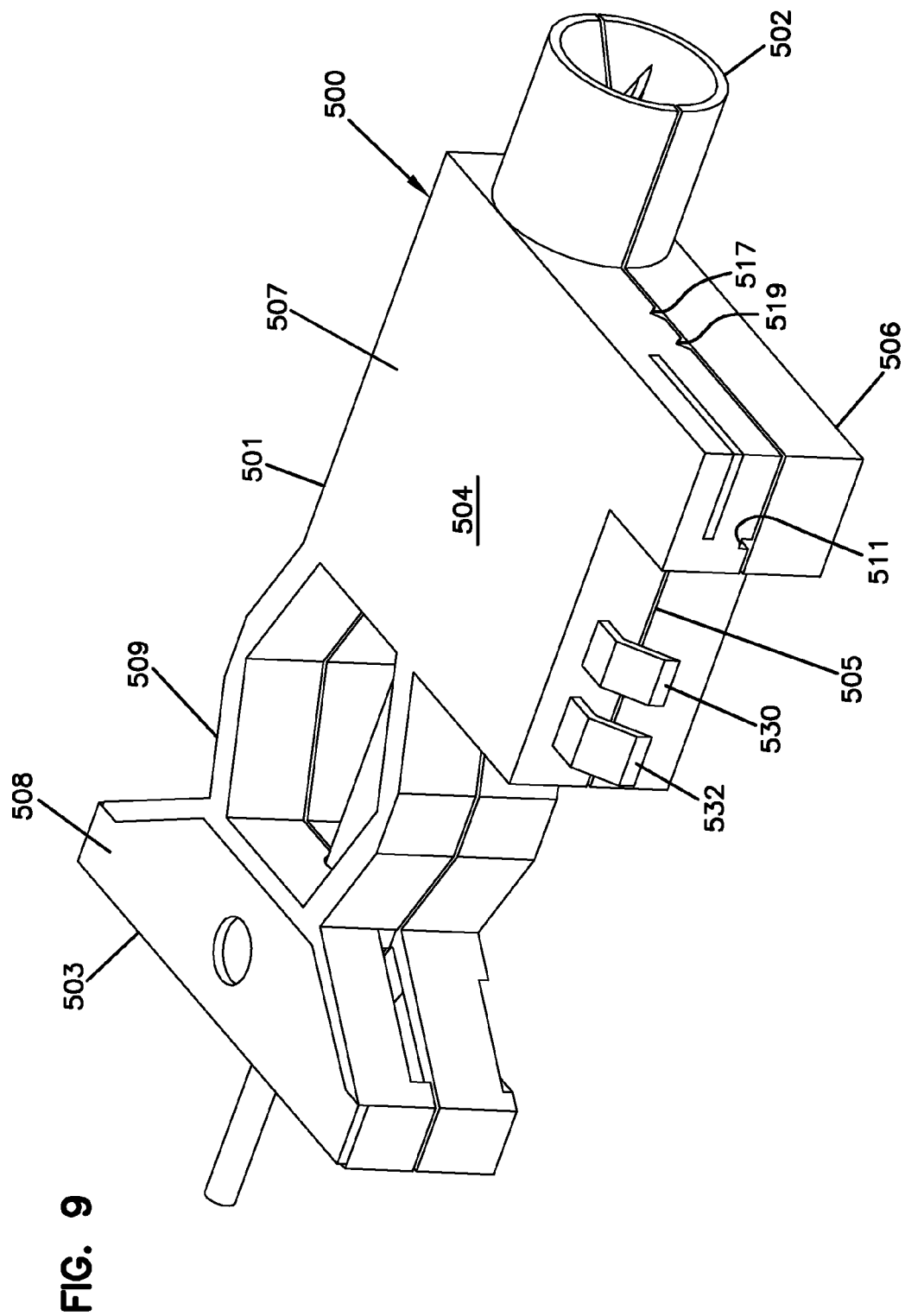
FIGS. 9 and 10 show another sensor module that can be manufactured in accordance with the principles of the present disclosure.

The first housing portion 410 of the first sensor module 400 is aligned with the second housing portion 420 in FIG. 6. In one embodiment, the protrusion 405 of the first housing portion 410 fits within the channel 426 of the second housing portion 426. Further, the first housing portion 410' of the second sensor module 400' is similarly aligned with the second housing portion 420' of the second sensor module 400'. In one embodiment, each sensor module 400, 400' defines a gap 460, 460' at which electrodes (e.g., see reference nos. 572, 574 of FIG. 9) can be coupled to the housing in contact with the electrodes.

Figure 7:
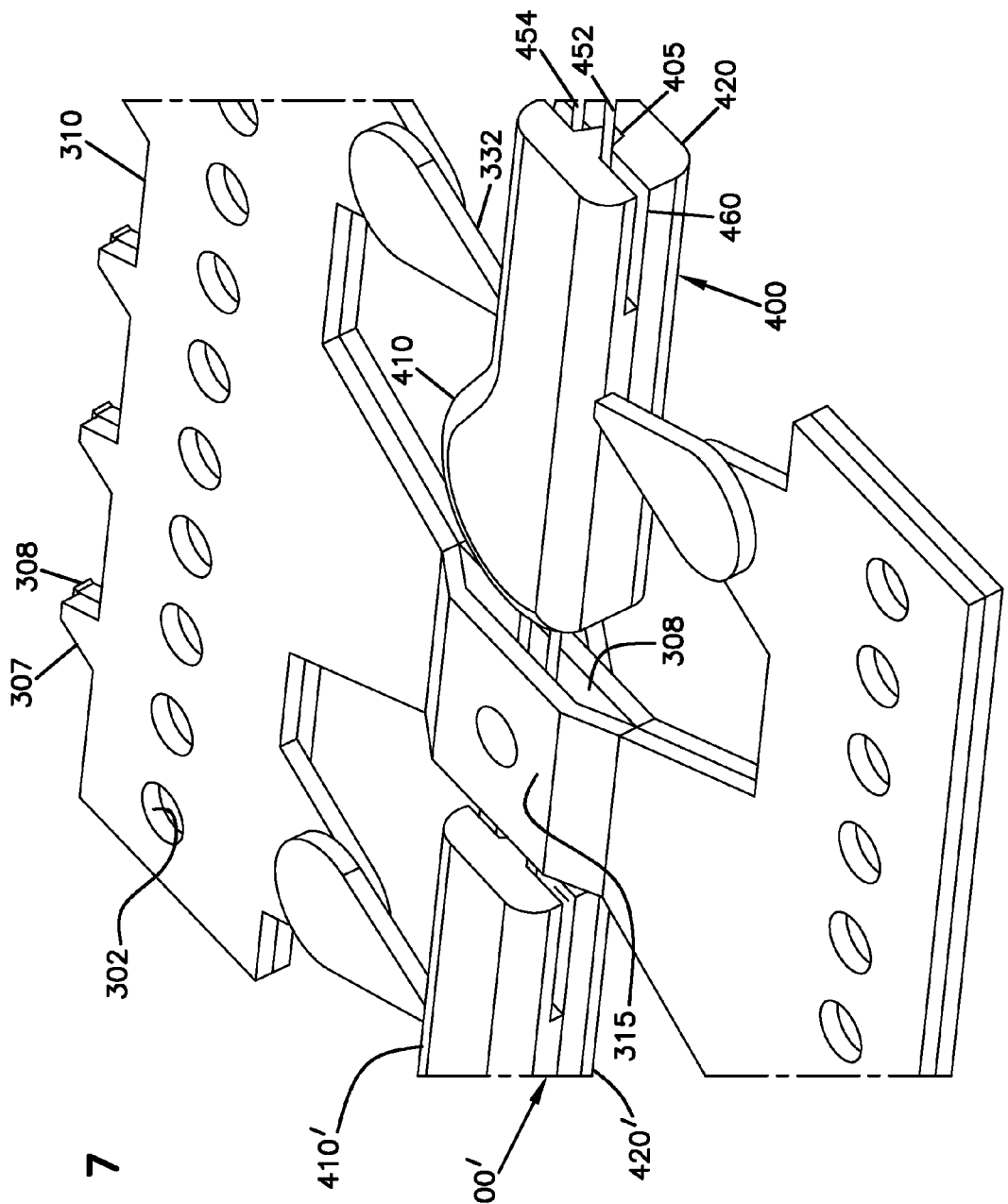
FIG. 7 is a partial, perspective view of the opposite side of the portion of the carrier of FIG. 6 after the opposing components have been secured together in accordance with the principles of the present disclosure.

FIG. 7 is an isometric view of the opposite side of the portion of the carrier 101 shown in FIG. 6 after the opposing components have been secured together (e.g., at joining station 150 of FIG. 1). The carrier body 300 has been broken in half at the centers 308 of the connecting members 307. The index holes 302 of the first and second sections 310, 320 of the carrier body 300 align. The first and second housing portions 410, 420 of the first sensor module 400 also are visibly aligned with each other. When the first housing portion 410 is aligned with the second housing portion 420, the depressions 415, 425 defined in the housing portions 410, 420 form an analysis cell through which the electrodes 452, 454 pass. The groove 407 defined in the first housing portion 410 forms a sample path extending from the analysis cell to an exterior of the sensor module 400. Fluid can be provided to the analysis cell, and hence the portion of the electrodes 452, 454 extending through the analysis cell, through capillary action or wicking.

Furthermore, the first and second housing portions 410, 420 are joined together (e.g., via a weld, an overmold layer, or another joining structure). In a preferred embodiment, the housing portions 410, 420 are secured together using a selective laser weld. For example, in one embodiment, the second housing portion 420, which does not contain active components, such as the electrodes 452,454, is transparent to the laser while the first housing portion 410, which contains the electrodes, is absorptive to the laser energy, thereby establishing an interior plane for a precise laser weld creating a hermetic seal for the analysis cell and related component structures.

Figure 8:
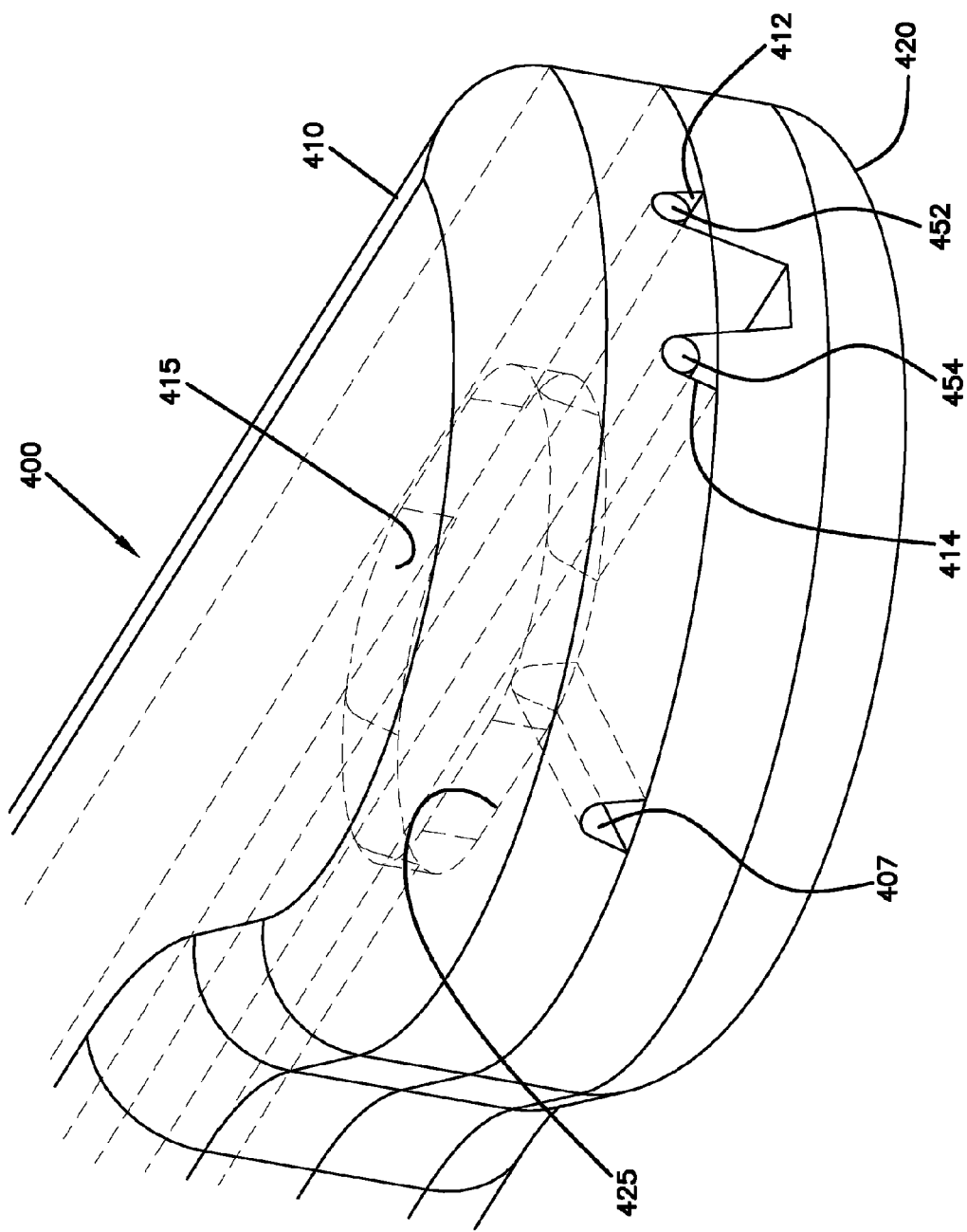
FIG. 8 is a partial, isometric view of the first sensor module of FIG. 7 after the sensor module has been separated from the carrier in accordance with the principles of the present disclosure.

FIG. 8 is a partial, isometric view of the first sensor module 400 after the sensor module 400 has been separated from the carrier 101 (e.g., at the separation station 160 of FIG. 1). The first housing portion 410 is shown as transparent in FIG. 1 so that the interior configuration of the sensor module 400 is visible. The electrodes 452, 454 extend through the channels 412, 414 defined in the first housing and through the analysis cell formed by the depressions 415, 425. In FIG. 8, the electrodes 452,454 terminate at the periphery of the housing.

FIGS. 9-15 walk through another application in which another example sensor module 500 (see FIGS. 9 and 10) is manufactured in accordance with the principles of the present disclosure. For example, the sensor module 500 can be fabricated using the manufacturing system 100 of FIG. 1 and/or the manufacturing process 200 of FIG. 2. The sensor module 500 includes a module body 501 having a distal end 502 positioned opposite from a proximal end 503. The module body 501 includes a first housing portion 504 secured to a second housing portion 506 at a part line 506.

The module body 501 includes an analysis cell housing 507 positioned adjacent the distal end 502 and a skin piercing member anchor 508 positioned adjacent the proximal end 503. A flexible linkage 509 mechanically connects the analysis cell housing 507 to the skin piercing member anchor 508. The flexible linkage 509 is configured to allow the analysis cell housing 507 and the skin piercing member anchor 508 to move relative to one another along an axis A that extends through the module body 501 from the proximal end 503 to the distal end 502 (see FIG. 10).

The skin piercing member anchor 508 is configured to slideably secure a skin piercing member (e.g., a cannula, a needle, a lancet, or other structure) 518 within an axially extending passage 514 defined in the analysis cell housing 507. The flexible linkage 509 of the module body 501 preferably has a compressible configuration that enables the flexible linkage 509 to compress axially along the axis A as the skin piercing member anchor 508 moves the skin piercing member 518 from a retracted position to an extended position to pierce the skin of the patient and obtain a fluid sample (e.g., a blood sample).

The analysis cell housing 507 defines an analysis cell 512 (FIG. 10) at which the fluid sample can be analyzed using a sensor structure, such as a wired enzyme sensor arrangement, in fluid communication with the analysis cell 512. The analysis cell 512 has a first end in fluid communication with a capillary slot 513 leading to the passage 514 and an opposite, second end at which a vent 511 is defined. The passage 514 includes a distal end 515 positioned opposite from a proximal end 516 and is configured to transport a fluid sample from a distal end 502 of the module body 501 to the analysis cell 512.

The analysis cell housing 507 also defines first and second electrode mounting structures (e.g., V-grooves) 517, 519 extending from a proximal end of the analysis cell housing to a distal end. First and second electrodes (not shown) extend within the mounting structures 517, 519 across the analysis cell 512 to contact receivers (e.g., receptacles, pads, slots, or other structures) 534, 536 for receiving and retaining electrode contacts 530, 532 (see FIG. 10). The contacts 530, 532 include exposed tips protruding outwardly from the analysis cell housing 507 to enable transmission of signals generated by the electrodes to metering electronics.

Additional details on the sensor module 500, monitoring and delivery systems utilizing the sensor module 500, and monitoring and delivery processes that can be implemented using the sensor module 500 can be found in copending application no. 61/114,844, filed Nov. 14, 2008, the disclosure of which is hereby incorporated by reference herein.

Figure 11:
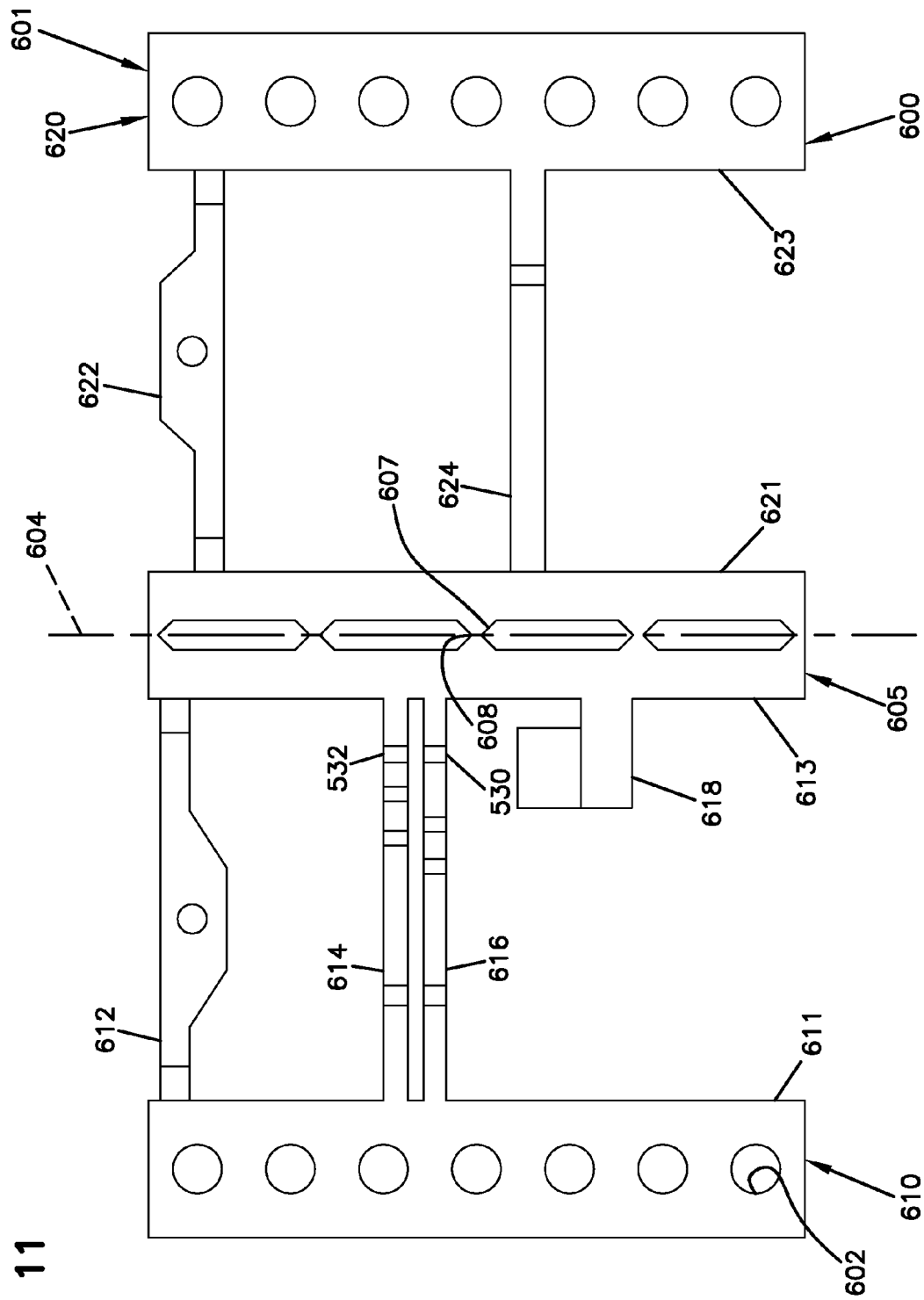
FIG. 11 is a planar view of a portion of another example carrier that can be indexed through the processing stations of the manufacturing system of FIG. 1 in accordance with the principles of the present disclosure.

Referring to FIGS. 11-15, the first and second housing portions 504, 506 of the sensor module 500 can be molded on opposite sides of a carrier, such as the carrier 600 of FIG. 11. FIG. 11 shows a portion of one example carrier 600 that can be indexed through the different processing stations 110, 120, 130, 140, 150, 160 of the manufacturing system 100 of FIG. 1. The carrier 600 includes a generally flat carrier body 601 defining a profile that is configured to support the components of the sensor module to be manufactured. One or more components can be molded to the carrier body 601 as the carrier 600 is indexed. In certain embodiments, multiple components of one sensor module can be molded across the carrier body 601.

The carrier body 601 also defines at least one series of index holes 602 configured to receive index pins to advance the carrier through a manufacturing system. In the example shown, the carrier body 601 defines two series of index holes 602. In other embodiments, however, the carrier body 601 can define greater or fewer series of index holes 602. In a preferred embodiment, the carrier body 601 is produced by roll stamping a high-precision profile on a stainless steel or suitable polymer tape and storing the prepared tape on a collector reel, such as the first carrier reel 102 of FIG. 1.

The carrier body 601 includes a fold feature 605 that splits the carrier body 601 into a first section 610 and a second section 620 along a fold axis 604. Folding the carrier body 601 along the fold axis 604 aligns the first section 610 with the second section 620. Accordingly, the fold feature 605 of the carrier body 601 enables opposing portions of sensor components to be molded onto the first and second sections 610, 620 of the carrier body 601 and subsequently assembled together by folding the carrier body 601 along the fold axis 604.

In general, the fold feature 605 is a weakened or reduced portion of the carrier body 601 at which the carrier body 601 is configured to bend and/or break. In the example shown, the fold feature 605 includes multiple connecting members 607 extending between the first and second sections 610, 620. The connecting members 607 have a tapered center 608 that is configured to bend to enable the carrier body 601 to be folded at the fold feature 605. In a preferred embodiment, the fold feature 605 of the carrier body 601 is a midline fold feature that splits the carrier body 601 along a central axis into two halves. In other embodiments, however, the fold feature 605 can split the carrier body 601 into sections 610, 620 of different sizes.

The carrier body 601 shown in FIG. 11 has a profile configured to support at least two molded components of a sensor module. Each section 610, 620 includes a first support wall 611, 621 and a second support wall 613, 623. One or more support members extend inwardly from the support walls 611, 613, 621, 623 of the each section 610, 620, respectively. The support members are configured to provide support for molded components of the sensor module. The sensor components are molded onto the support members between the support walls 611, 613, 621, 623.

For example, in FIG. 11, the first section 610 includes a first support member 612 extending between the support walls 611, 613 at a first end of the carrier profile. The first section 610 also includes second and third support members 614, 616 extending between the support walls 611, 613 at a position spaced from the first support member 612. A fourth support member 618 also extends inwardly from the second support wall 613. The second section 620 includes a first support member 622 extending between the support walls 621, 623 at the first end of the carrier profile and a second support member 624 extending between the support walls 621, 623 at a position spaced from the first support member 622.

Figure 12:
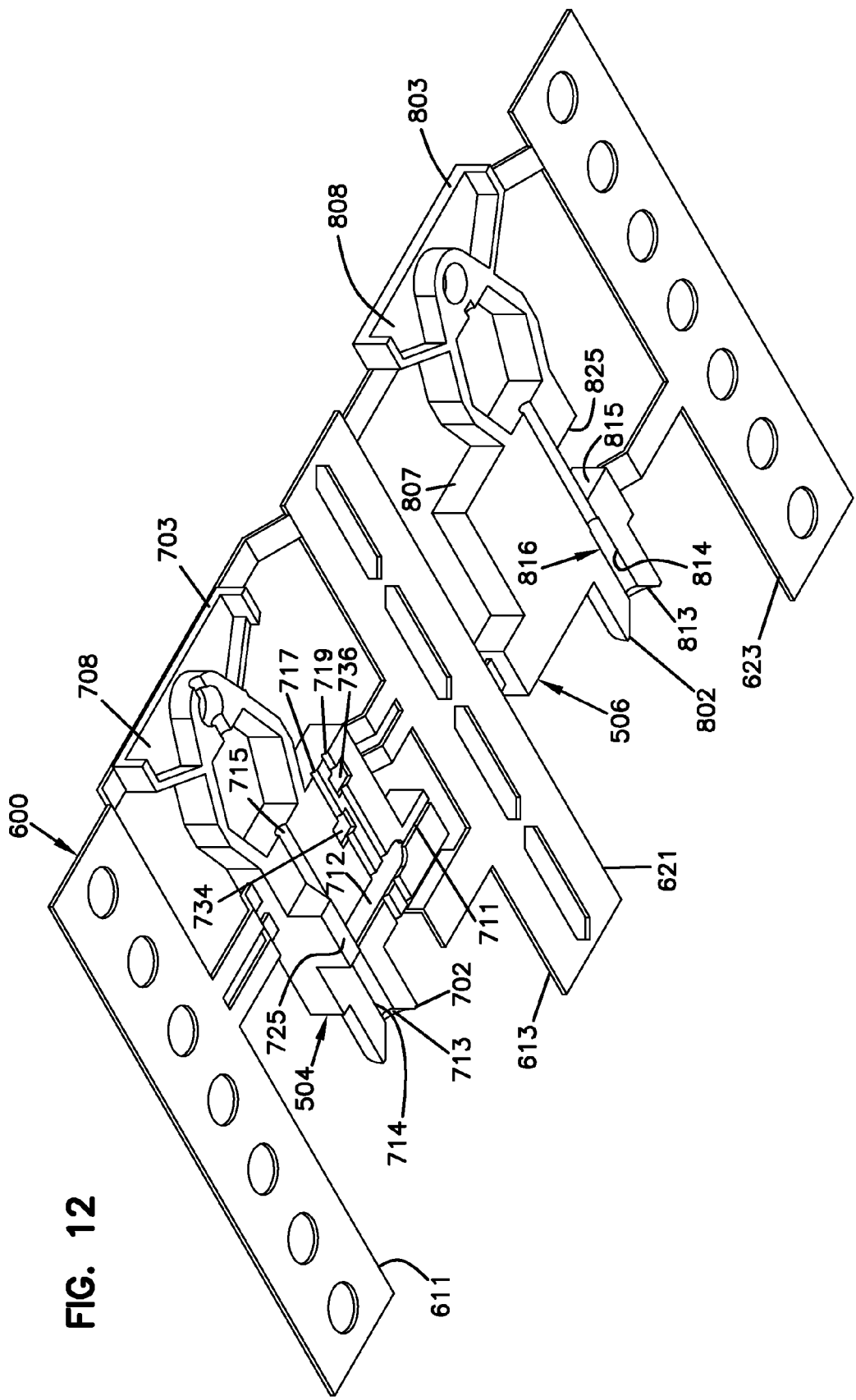
FIG. 12 is a top, perspective view of the portion of the carrier of FIG. 11 after sensor module components have been molded onto the body of the carrier in accordance with the principles of the present disclosure.

FIG. 12 shows the portion of carrier 600 of FIG. 11 after sensor module components have been molded onto the body 601 of the carrier 600 (e.g., at the mold station 110 of FIG. 1). In the example shown, components of a single sensor module 500 have been molded onto the visible portion of the carrier body 601. A first housing portion 504 has been molded onto the support members 612, 614, 616, 618 of the first section 610 of the carrier 600. A second housing portion 506 has been molded onto the support members 622, 624 of the second section 620 of the carrier 600. The first housing portion 504 is formed to be generally complementary to the second housing portion 506.

Each housing portion 504, 506 includes an analysis cell housing section 707, 807, a flexible linkage section 709, 809, and an anchor section 708, 808, respectively. In one embodiment, the analysis cell housing section 707 of the first housing portion 504 defines a depression 712 that at least partially forms the analysis cell 512 when the housing portions 504, 506 are subsequently joined together. In one embodiment, the analysis cell 512 is fully defined by the depression 712 in the analysis cell housing section 707. In another embodiment, a corresponding depression (not shown) is formed in the analysis cell housing section 807 of the second housing portion 506. In the example shown in FIG. 12, a channel 711 extends from the depression 712 to an exterior of the first housing portion 504. In a some embodiment, the depression 712 is about 0.01 inches (0.25 millimeters) to about 0.05 inches (1.27 millimeters) across at a largest dimension and about 0.002 (0.05 millimeters) to about 0.005 inches (0.13 millimeters) deep. In a preferred embodiment, the depression 712 is about 0.03 inches (0.76 millimeters) across at the largest dimension and about 0.003 (0.08 millimeters) deep.

The first and second housing portions 504, 506 each define a channel 716, 816 that extends between proximal and distal ends 702, 703, 802, 803 of the housing portion 504, 506, respectively. When the housing portions 504, 506 are subsequently joined together, the channels 716 and 816 form the passageway 514 through which a fluid sample can be transported to the analysis cell 512. In other embodiments, the passageway 514 can be formed entirely by the channel 716 within the first housing portion 504 or the channel 816 within the second housing portion 506.

Each channel 716, 816 includes a first section 713, 813, a second section 714, 814, and a third section 715, 815, respectively. The first sections 713, 813 of the channels 716, 816 have a frustro-conical shape configured to allow blood or other fluid to enter the passageway 514 formed by the channels 716, 816. The second section 714, 814 of the channels 716, 816 extend between the first sections 713, 813 and the depression 712. The third sections 715, 815 of the channels 716, 816 extend from the depression 712 to the opposite end of the analysis cell housing section 707, 807.

Figure 10:
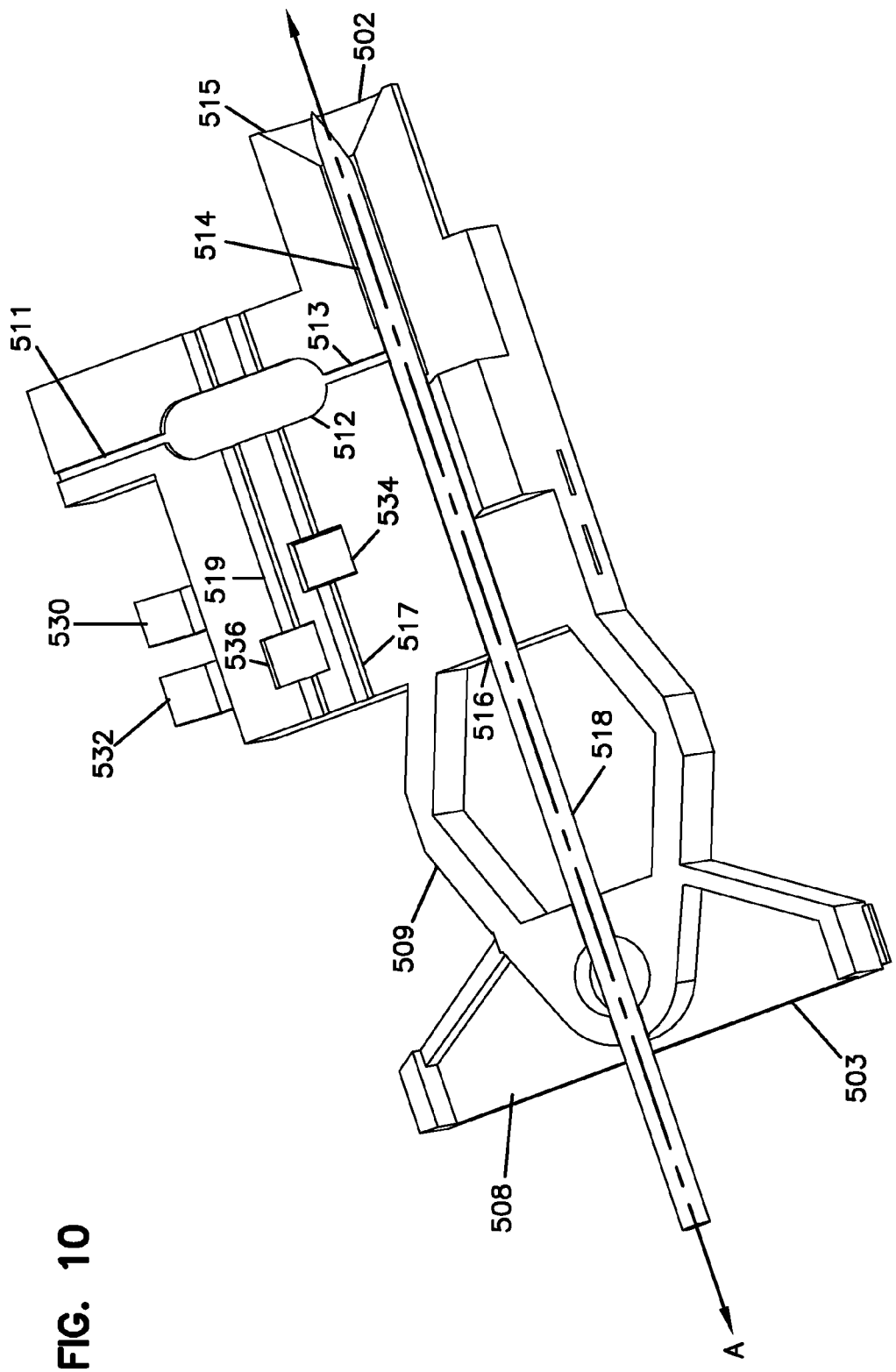

The second sections 714, 814 have diameters generally sufficient to enable sliding movement of a piercing member, such as piercing member 518 of FIG. 10, and to enable passage of a sample fluid alongside the piercing member 518. The third sections 715, 815 have diameters that are less than the diameters of the second sections 714, 814. In one embodiment, the diameters of the third sections 715, 815 are sized to enable sliding movement of the piercing member 518, but to inhibit passage of a sample fluid alongside the piercing member 518.

The analysis cell housing section 707 of the first housing portion 504 also can define electrode channels 717, 719 in which first and second continuous electrodes (not shown) can be routed through the analysis cell housing section 807. In one embodiment, the electrode channels 717, 719 are V-shaped channels. In other embodiments, however, the channels 717, 719 can have any suitable shape (e.g., U-shaped, squared, etc.). In certain embodiments, corresponding electrode channels 717, 719 can be defined in the second housing portion 506.

In one embodiment, the analysis cell housing section 707 of the first housing portion 504 defines cavities or slots 734, 736 at which the electrodes are exposed to contact 530, 532 extending through the analysis cell housing section 707. These contacts 530, 532 include exposed tips that extend outwardly from the first housing portion 504 to enable electrical coupling to processing and/or metering electronics. Accordingly, signals generated at the electrodes can be forwarded to such electronics via the contacts 530, 532.

In some embodiments, these contacts 530, 532 can be coupled to the carrier 600 on which the housing portions 504, 506 are molded prior to the manufacturing process. For example, in FIG. 11, the contacts 530, 532 are coupled to support members 614, 616 of the first section 610 of the carrier 600. Accordingly, the first housing portion 504 can be overmolded around the contacts 530, 532 to embed the contacts 530, 532 in the first housing portion 504. In other embodiments, however, these contacts 530, 532 are inserted into the slots 734, 736 at the completion of the manufacturing process.

In some embodiments, one or both housing portions 504, 506 also can include attachment members configured to secure the housing portions 504, 506 together. For example, one of the housing portions 504, 506 can include a peg or other protrusion configured to mate with an opening, depression, or groove, or slot defined in the other of the housing portions 504, 506. In one embodiment, the first housing portion 504 defines an extended protrusion 725 that is configured to fit within a corresponding slot 825 defined in the second housing portion 506 (e.g., see FIG. 13).

Figure 13:
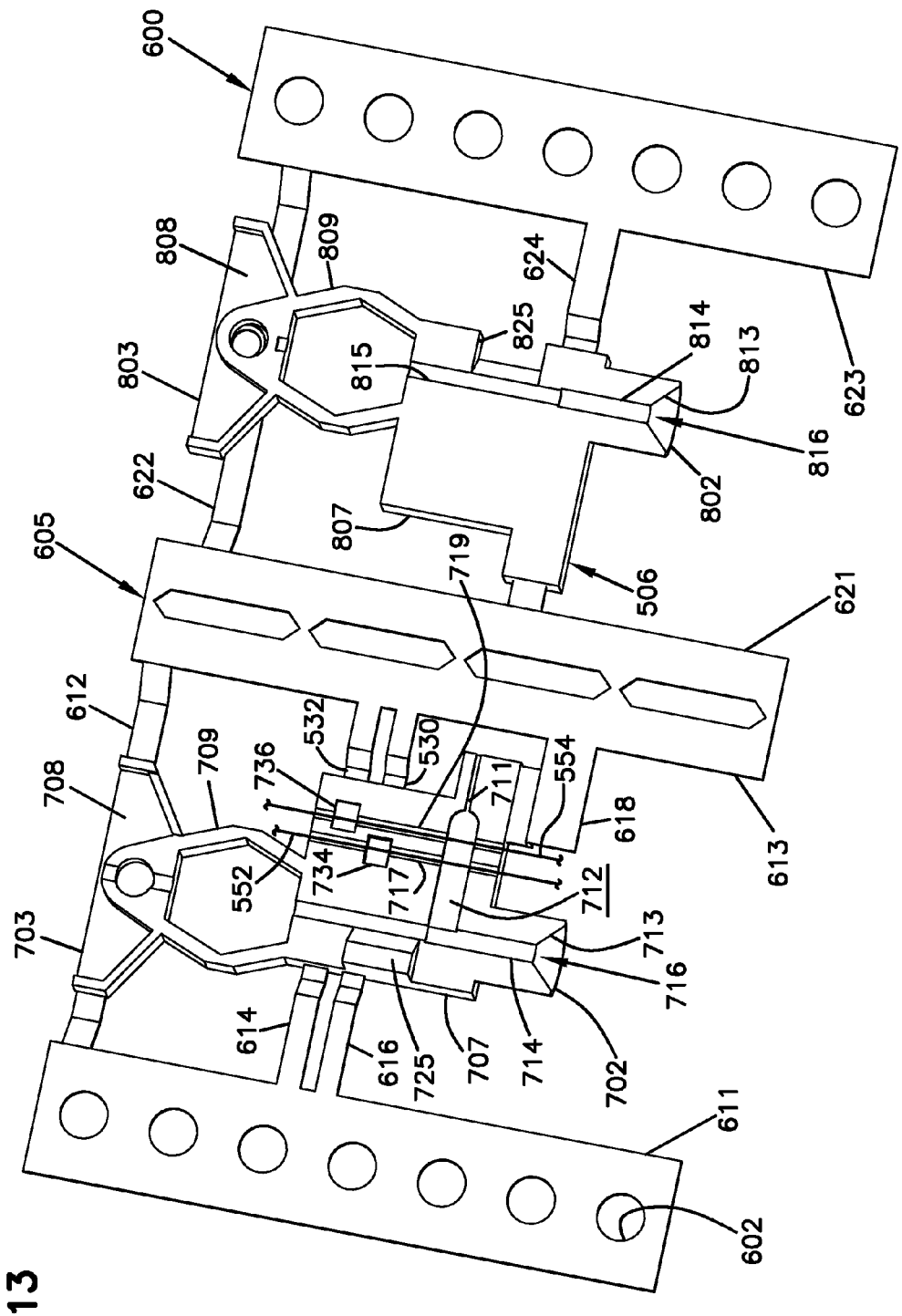
FIG. 13 is a planar view of the portion of the carrier of FIG. 12 after a first electrode and a second electrode have been routed onto the molded sensor components in accordance with the principles of the present disclosure.

FIG. 13 shows the portion of the carrier 600 of FIG. 12 after a first electrode 552 and a second electrode 554 have been routed onto the molded sensor components (e.g., at the insertion station 130 of FIG. 1). In the example shown, the electrodes 552,554 are routed through channels 717, 719 of the first housing portion 504. Accordingly, the electrodes 552, 554 pass through the depression 712 partially forming the analysis cell 512. Typically, the first electrode 552 is a working electrode formed by coating sensor chemistry onto an elongated member and the second electrode 554 is a reference electrode formed from an uncoated elongated member.

Figure 14:
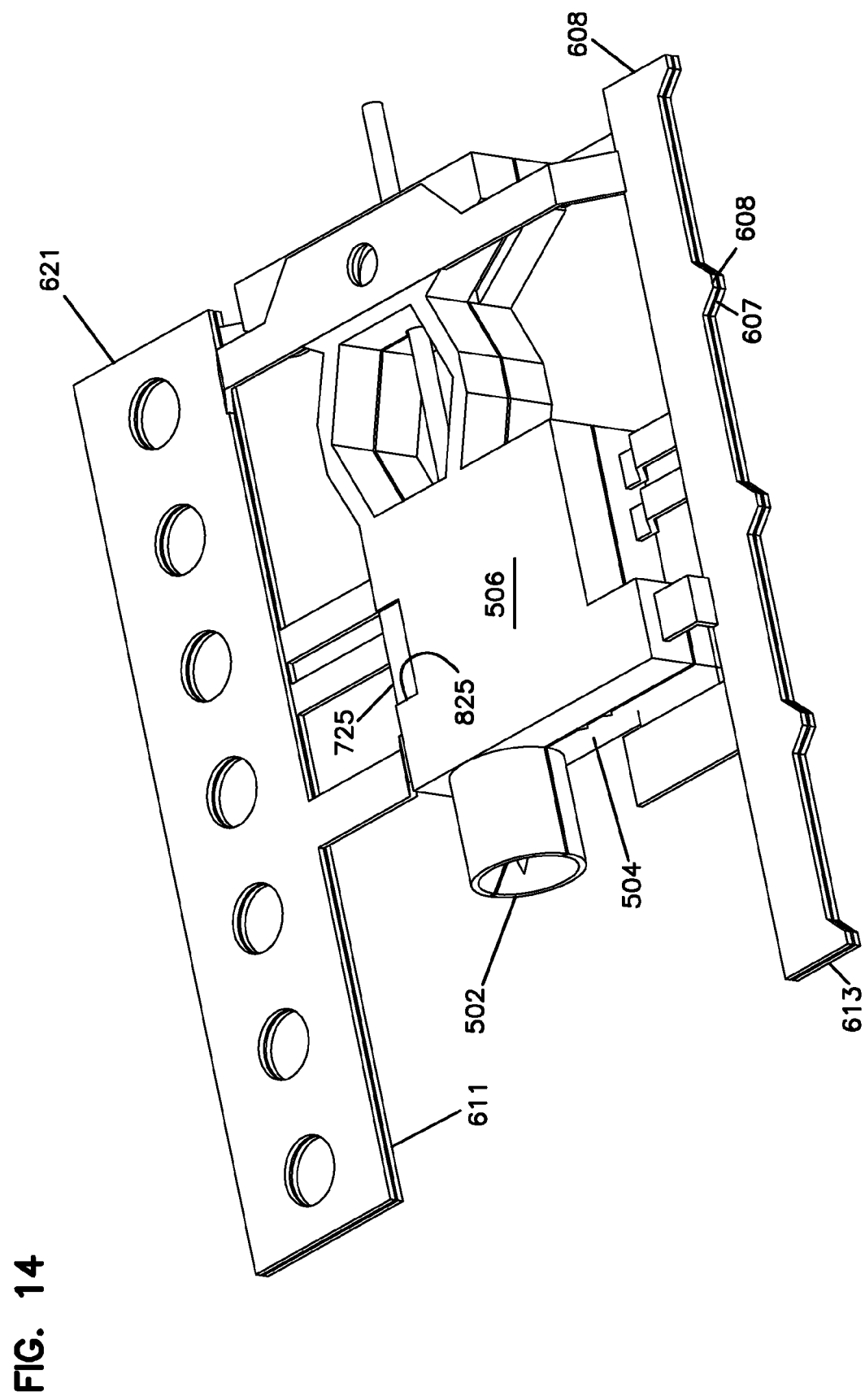
FIG. 14 is a perspective view of the portion of the carrier of FIG. 13 after the carrier has been folded along a fold axis to align the first and second sections of the carrier body in accordance with the principles of the present disclosure.

FIG. 14 is an isometric view of the portion of the carrier 600 after the carrier 600 has been rolled or folded along the fold axis 605 (FIG. 11) to align the first and second sections 610, 620 of the carrier body 600 (e.g., at fold station 140 of FIG. 1). In one embodiment, the connecting members 607 extending between the first and second sections 610, 620 of the carrier body 600 are broken at their tapered centers 608 along the fold axis 604 as shown in FIG. 14. In other embodiments, however, the connecting members 607 bend sufficiently to enable the first section 610 to align with the second section 620 without breaking the carrier 600 into two sections.

The first housing portion 504 of the sensor module 500 is aligned with the second housing portion 506 in FIG. 14. In one embodiment, the protrusion 725 of the first housing portion 504 fits within the slot 825 of the second housing portion 506. When the first housing portion 504 is aligned with the second housing portion 506, at least the depressions 712 defined in the first housing portion 504 forms an analysis cell 512 through which the electrodes 552, 554 pass. The channels 716, 816 defined in the first and second housing portions 504, 506 form the sample path 514 extending through the analysis cell 512. Fluid can be provided to the analysis cell 512, and hence the portion of the electrodes 552, 554 extending through the analysis cell, through capillary action or wicking.

The first and second housing portions 504, 506 are joined together (e.g., via a weld, an overmold layer, or another joining structure). In a preferred embodiment, the housing portions 504, 506 are secured together using a selective laser weld. For example, in one embodiment, the second housing portion 506, which does not contain active components, such as the electrodes 552, 554, is transparent to the laser while the first housing portion 504, which contains the electrodes 552, 554, is absorptive to the laser energy, thereby establishing an interior plane for a precise laser weld creating a hermetic seal for the analysis cell and related component structures.

Figure 15:
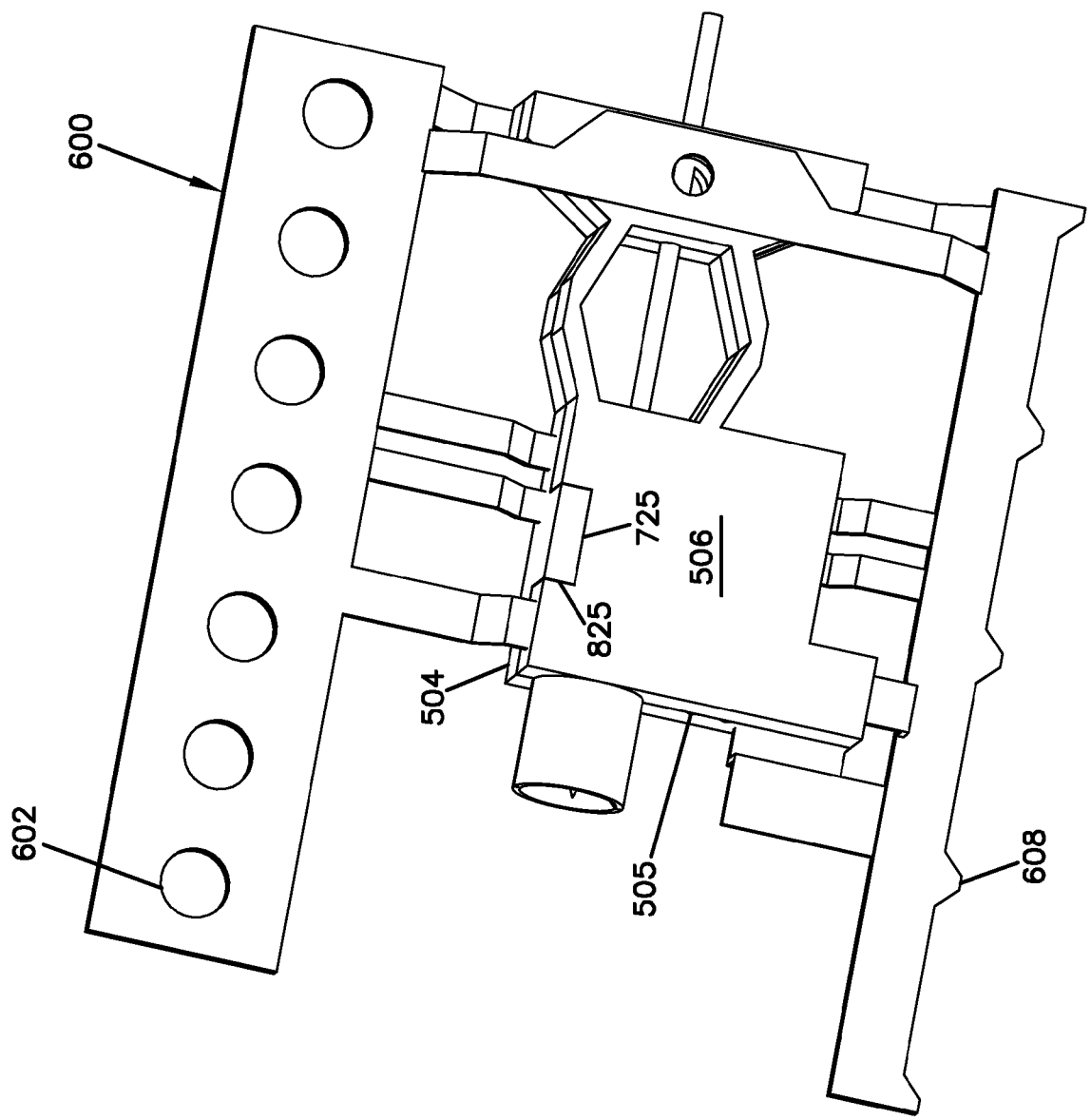
FIG. 15 is a perspective view of the opposite side of the portion of the carrier of FIG. 15 after the opposing components have been secured together in accordance with the principles of the present disclosure.

FIG. 15 is an isometric view of the portion of the carrier 600 shown in FIG. 14 after the opposing components have been secured together (e.g., at joining station 150 of FIG. 1). The carrier body 600 has been broken in half at the centers 608 of the connecting members 607. The index holes 602 of the first and second sections 610, 620 of the carrier body 600 align. The first and second housing portions 504, 506 of the sensor module 500 also are visibly aligned with each other.

Additional features can be added to the interior of the sensor modules 400, 500 after the support components are molded on the carrier body 300, 600 and prior to folding the carrier body 300, 600. For example, in certain embodiments, a piercing member (e.g., needle cannula 518 of FIG. 10) can be added to the sensor module (e.g., sensor module 500 of FIGS. 9 and 10) to aid in obtaining a fluid sample. In other embodiments, additional features can be added to the sensor module after completion of the manufacturing process (e.g., manufacturing process 200 of FIG. 2). For example, in certain embodiments, an reservoir containing insulin or another drug can be added to the sensor module after the sensor module has been separated from the carrier. Of course, the piercing member also can be added to the sensor module after separation from the carrier.

Additional details regarding example sensor modules that can be manufactured using the systems and processes disclosed herein can be found in copending application Ser. Nos. 61/114,829 and 61/114,844, filed Nov. 14, 2008, the disclosures of which are hereby incorporated herein by reference.

Figure 16:
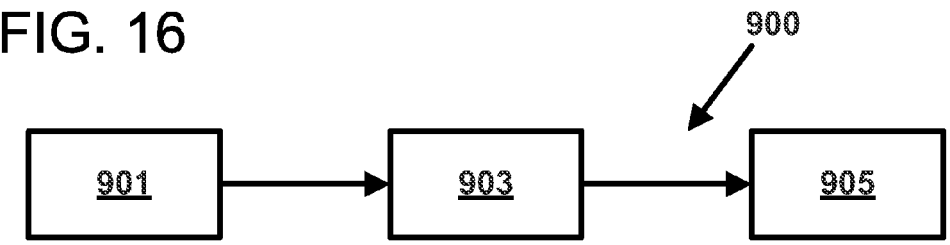
FIG. 16 illustrates another manufacturing system by which sensor modules may be assembled.

FIG. 16 illustrates another manufacturing system 900 by which sensor modules may be assembled. In some implementations, all of the components of the sensor 908 are assembled to form a first housing portion 902 and a second housing portion 904. In some implementations, the first and second housing portions 902, 904 form first and second halves of the sensor module 908. In other implementations, the first housing portion 902 forms more or less than half of the sensor module body. At least one of the housing portions 902, 904 defines an inlet, a test chamber, and passages therebetween. A skin-piercing member is positioned on one of the housing portions 902, 904.

In some implementations, the manufacturing system 900 includes a first station 901 for depositing electrodes (e.g., composite sensor fibers) onto the first housing portions 902, a second station 903 for joining the housing portions 902, 904, and a third station 905 for separating the joined housings from each other to form the sensor modules 908. Of course, in other implementations, the same station may perform some or all of these processes. In some implementations, the sensor components may be positioned on one or more conveyor belts 912, fluid streams, pallets or other transportation structures to convey the components through the manufacturing system.

Figure 17:
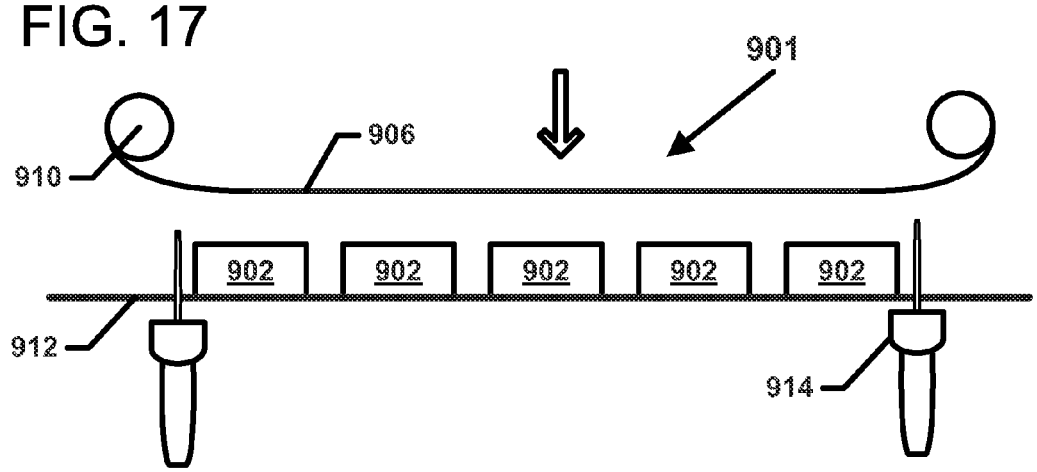
FIG. 17 illustrates one example implementation of a first station of the manufacturing system of FIG. 16 that is configured to deposit one or more composite sensor fibers onto the first housing portion of one or more sensor modules.

FIG. 17 illustrates one example implementation of a first station 901 of the manufacturing system 900. The first station 901 is configured to deposit one or more sensor fibers 906 onto the first housing portion 902 of one or more sensor modules 908. In one example implementation, the sensor fiber includes a composite sensor fiber having a dielectric core, a conductive layer, and a sensing layer. In some implementations, the first station 901 deposits a single sensor fiber 906 onto each first housing portion 902. In other implementations, the first station 901 deposits multiple sensor fibers 906 onto each first housing portion 902. For example, the first station 901 may deposit a working electrode and a counter electrode onto each first housing portion 902.

In some implementations, the first station 901 dispenses the composite sensor fibers 906 onto a single first housing portion 902 on each duty cycle. In other implementations, the first station 901 dispenses the composite sensor fibers 906 onto multiple first housing portions 902 on each duty cycle. In the example shown, the first station 901 dispenses the composite sensor fibers 906 onto five first housing portions 902 on each duty cycle. In other implementations, the first station 901 may dispense the composite sensor fibers 906 onto greater or fewer housing portion 902 on each duty cycle.

In some implementations, the composite sensor fibers 906 are dispensed from one or more reels 910 into channels defined in the first housing portions 902. In certain implementations, the first station 901 includes a first set of reels 910 that dispense the composite sensor fibers 906 onto a first row of first housing portions 902. In other implementations, the first station 901 includes multiple sets of reels 910, each set dispensing sensor fibers 906 onto a row of first housing portions 902.

In certain implementations, the first station 901 also includes one or more cutting structures 914 that disconnect the dispensed sensor fibers 906 from the reels 910. In some implementations, the cutting structures 914 cut the sensor fibers 906 at extreme ends of the set of first housings 902. In such implementations, a continuous length of each sensor fiber 906 extends through all of the first housing portions 902 at the first station 901. In other implementations, the cutting structures 914 cut the sensor fibers 906 to separate the sensor fibers 906 of each first housing portion 902.

Figure 18:
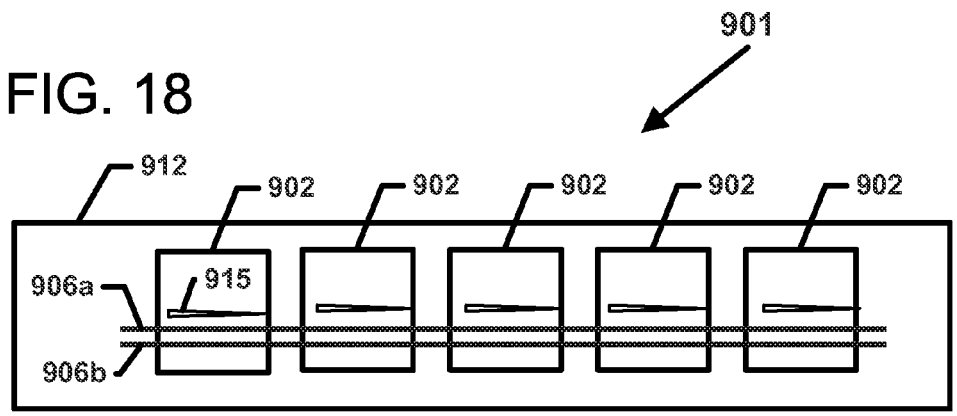
FIGS. 18 and 19 are top plan views of example implementations of the first station of FIG. 17.
Figure 19:
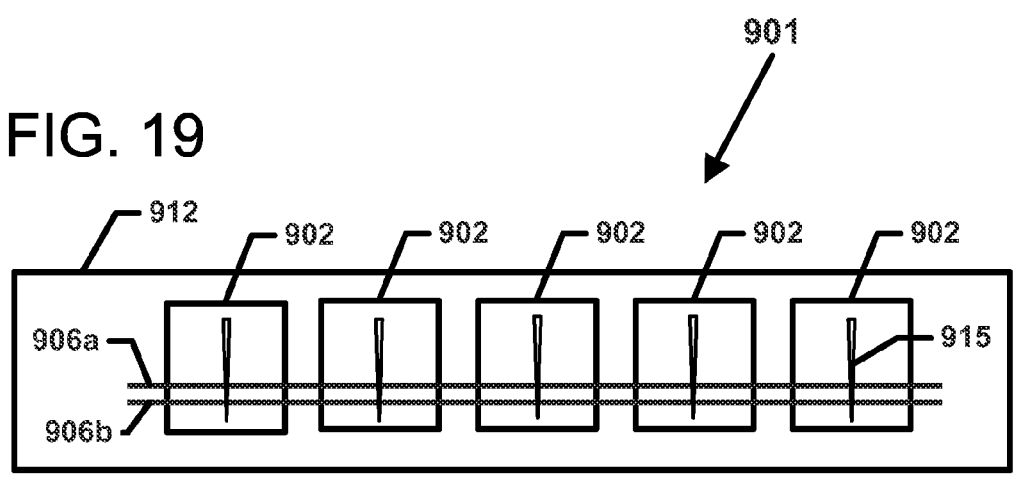

FIGS. 18 and 19 are top plan views of example implementations of the first station 901 of FIG. 17. The first station 901 includes a conveyer 912 on which multiple first housing portions 902 are positioned. In certain implementations, each first housing portion 902 includes a skin-piercing member (e.g., a lancet, a needle, etc.) 915. In other implementations, the skin-piercing member 915 is positioned in a second housing portion 904. In the example station 901 shown in FIG. 18, the first housing portions 902 are oriented so that the sensor fibers 906 are dispensed generally parallel to a longitudinal axis of the skin-piercing members 915. In the example station 901 shown in FIG. 19, the first housing portions 902 are oriented so that the sensor fibers 906 are dispensed generally perpendicular to a longitudinal axis of the skin-piercing members 915.

Figure 20:
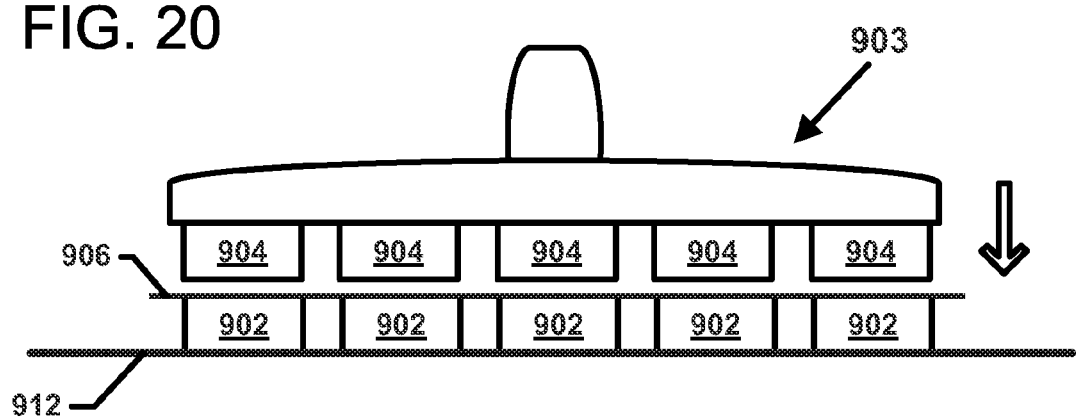
FIG. 20 illustrates one example implementation of a second station of the manufacturing system of FIG. 16 that is configured to join together a second housing portion to a first housing portion to enclose a skin-piercing member and one or more composite sensor fibers to form a sensor module.

FIG. 20 illustrates one example implementation of a second station 903 of the manufacturing system 900. The second station 903 is configured to join together a second housing portion 904 to a first housing portion 902 to enclose a skin-piercing member 915 and one or more composite sensor fibers 906 to form a sensor module 908. In some implementations, the second station 903 couples together the first and second housing portions 902, 904 of multiple sensor modules 908 per cycle. In other implementations, the second station 903 forms one sensor module 908 at a time.

In some implementations, the second station 903 may clamp the first and second housing portions 904 together. In other implementations, the second station 903 may weld together (e.g., sonic-weld or laser-weld) the first and second housing portions 904. In still other implementations, the second station 903 may press-fit or snap-fit the first and second housing portions 904 together. In still other implementations, the second station 903 may affix the first and second housing portions 904 together using adhesive.

In certain implementations, the continuous length of each sensor fiber 906 still extends through all of the housing portions 902, 904 at the second station 903 while the housing portions 902, 904 are coupled together. For example, the second station 903 may install a plurality of second housing portions 904 on a plurality of first housing portions joined along a continuous length of one or more composite sensor fibers 906. In the example shown in FIG. 20, the second station 903 is pressing five second housing portions 904 onto five first housing portions 902 that are connected by a continuous length of at least one electrode 906.

Figure 21:
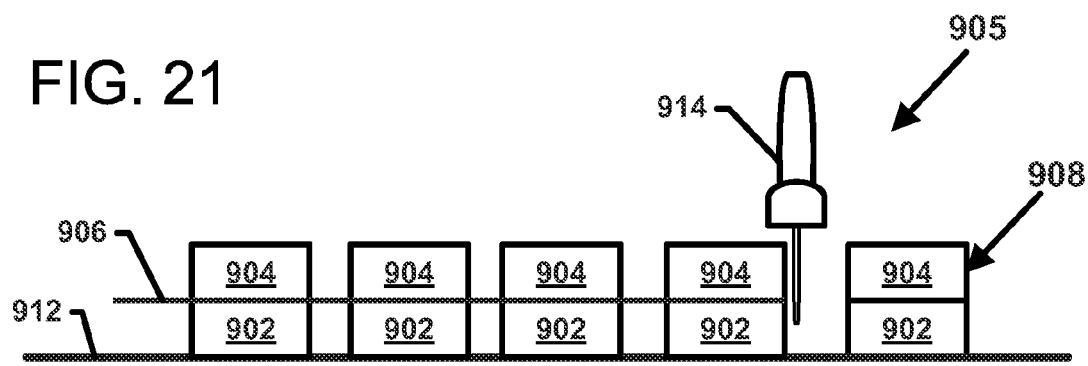
FIG. 21 illustrates one example implementation of a third station of the manufacturing system of FIG. 16 that is configured to separate the sensor modules from each other by cutting the continuous length of the one or more composite sensor fibers extending therebetween.

FIG. 21 illustrates one example implementation of a third station 905 of the manufacturing system 900. The third station 905 is configured to separate the sensor modules 908 from each other by cutting the continuous length of the one or more composite sensor fibers 906 extending therebetween. In some implementations, the sensor fibers 906 are cut with a laser. In other implementations, the sensor fibers 906 are cut with a knife. In other implementations, the sensor fibers 906 are cut with a nipper. In other implementations, the sensor fibers 906 are cut with pneumatic shears.

The third station 905 includes at least one cutting device 914. In some implementations, the third station 905 includes a single cutting device 914. For example, the third station 905 may be configured to cut the composite sensor fibers 906 at only one side of the module 908. In other implementations, the third station 905 includes multiple cutting devices 914. For example, the third station 905 may be configured to cut the composite sensor fibers 906 on both sides of the sensor module housing.

Figure 22:
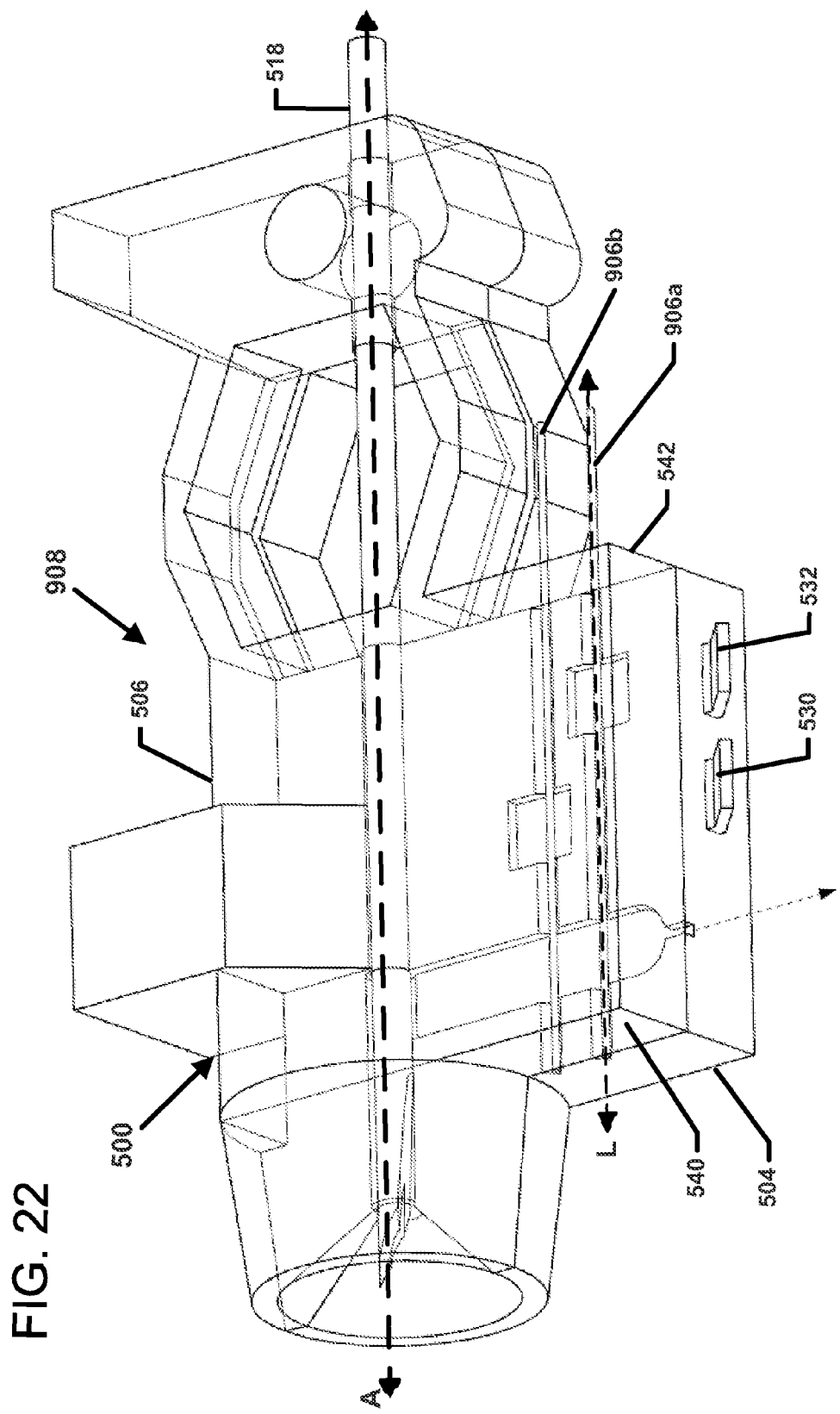
FIG. 22 shows one example sensor module with composite sensor fibers positioned between first and second housing portions parallel to a movement axis of a skin-piercing member.

In accordance with some aspects, the sensor module 500 of FIGS. 9-15 may be manufactured using the manufacturing system 900. For example, FIG. 22 shows the sensor module 500 with a first composite sensor fiber 906a and a second composite sensor fiber 906b positioned between the first and second housing portions 504, 506. The longitudinal axis L of each composite sensor fiber 906a, 906b extends generally parallel to the movement axis A of the skin-piercing member 518.

In accordance with certain aspects, the cut ends of the sensor fibers 906a, 906b are positioned at opposite surfaces 540, 542 of the housing 501. In some implementations, the opposite surfaces 540, 542 are located at extreme ends of the housing 501 (e.g., at opposite sides along the length of the housing 501 or at opposite sides along the width of the housing 501). In other implementations, the opposite surfaces 540, 542 are located on opposite sides of a portion of the housing 501. In the example shown in FIG. 22, the sensor fibers 906a, 906b have first cut ends at one side 540 of the analysis cell housing 507 and second cut ends at an opposite side 542 of the analysis cell housing 507.

As noted above, the sensor fiber contacts 530, 532 include exposed pads protruding outwardly from the analysis cell housing 507 to enable transmission of signals generated by the sensor fibers 906a, 906b to metering electronics. In some implementations, the exposed pads 530, 532 are located at the cut ends of the sensor fibers 906a, 906b. In other implementations, the exposed pads 530, 532 are located offset a distance from the cut ends of the sensor fibers 906a, 906b. In the example shown in FIG. 18, the contact pads 530, 532 extend from a surface transverse to the opposite surfaces 540, 542 at which the cut fiber ends terminate.

Figure 23:
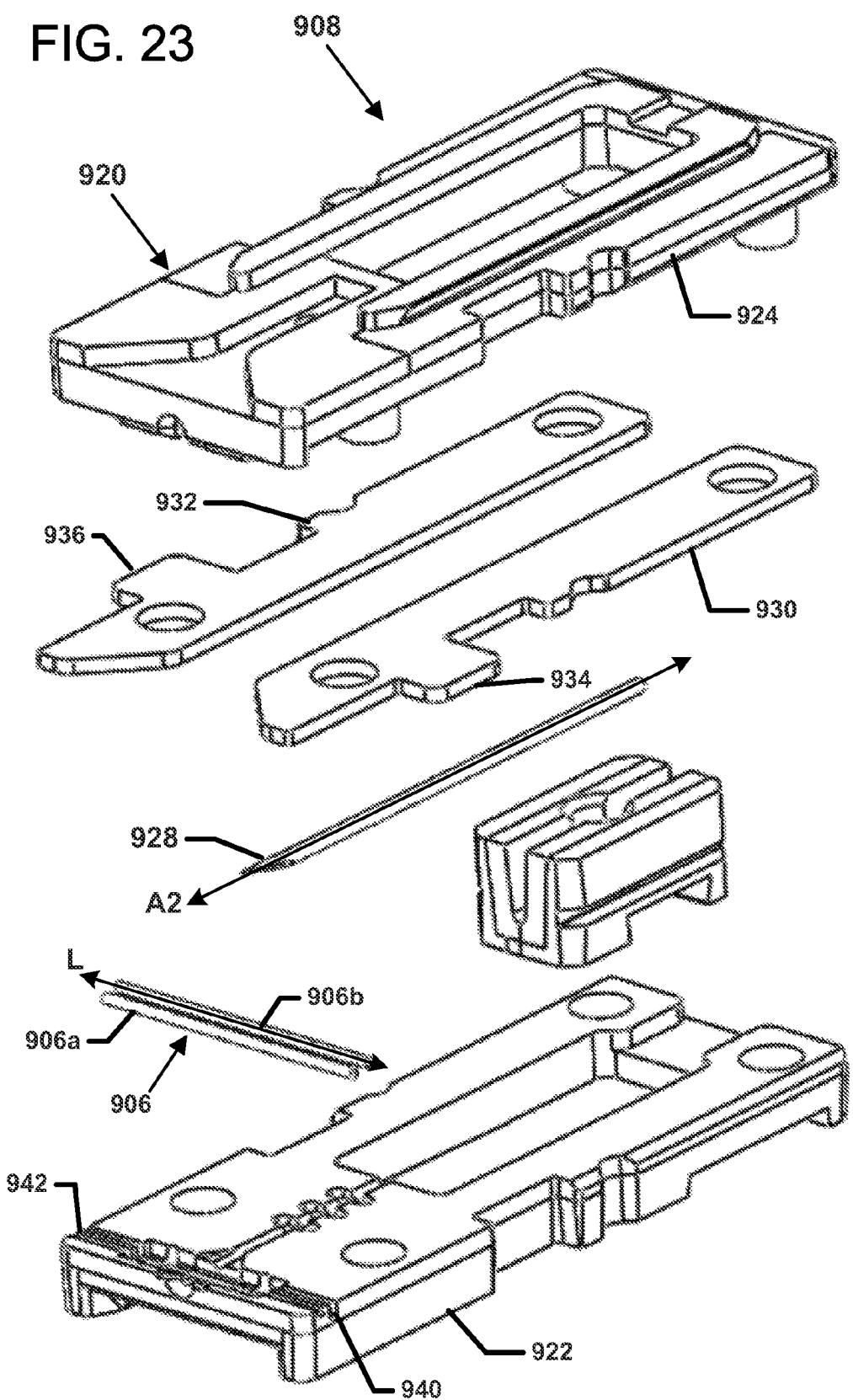
FIG. 23 shows another example sensor module with composite sensor fibers positioned between first and second housing portions perpendicular to a movement axis of a skin-piercing member.

In accordance with other aspects, another example sensor module 920 may be manufactured using the manufacturing system 900. For example, FIG. 23 shows the example sensor module 900 with a first composite sensor fiber 906a and a second composite sensor fiber 906b positioned between first and second housing portions 922, 924. The longitudinal axis L of each composite sensor fiber 906a, 906b extends generally perpendicular to a movement axis A2 of the skin-piercing member 928.

In accordance with certain aspects, the sensor fibers 906a, 906b extend from a first location at one surface 940 of the sensor 920 to a second location at an opposite surface 942 of the sensor 920. In some implementations, the opposite surfaces 940, 942 are located at extreme ends of the sensor module 920. In other implementations, the opposite surfaces 940, 942 are located on opposite sides of a portion of the sensor 920. In the example shown in FIG. 23, the sensor fibers 906a, 906b extend across a width of the sensor module 920 to opposite side surfaces 940, 942 at a front of the sensor module 920.

The sensor module 920 includes electrode contacts 930, 932 that connect to the composite sensor fibers 906a, 906b. In some implementations, the sensor fiber contacts 930, 932 include exposed pads 934, 936, respectively, protruding outwardly from the housing of the sensor module 920 to enable transmission of signals generated by the sensor fibers 906a, 906b to metering electronics. In some implementations, the exposed pads 934, 936 are located at the cut ends of the sensor fibers 906a, 906b. In other implementations, however, the exposed pads 934, 936 are offset from the cut ends of the sensor fibers 906a, 906b. In the example shown in FIG. 23, the contact pads 934, 936 are offset rearwardly along the opposite surfaces 940, 942 from the cut ends of the sensor fibers 906a, 906b.

Additional details regarding the sensor module 920 can be found in U.S. Provisional Application No. 61/430,384, filed Jan. 6, 2011, and titled "Sensor Module with Enhanced Capillary Flow," the disclosure of which is hereby incorporated herein by reference. Additional details regarding example sensor fibers suitable for use in sensor modules manufactured as described above can be found in U.S. Pat. Nos. 5,264,105; 5,356,786; 5,262,035; and 5,320,725, the disclosures of which are incorporated by reference herein. Further examples of sensor fibers are described in U.S. application Ser. Nos. 13/129,325, filed May 13, 2011, and titled "Electrochemical Sensor Module," the disclosure of which is incorporated by reference herein. Other examples of sensor fibers are described in PCT Publication Nos. WO 2009/032760 and WO 2009/051901, the disclosures of which are incorporated by reference herein.

The above specification provides examples of how certain aspects may be put into practice. It will be appreciated that the aspects can be practiced in other ways than those specifically shown and described herein without departing from the spirit and scope of the present disclosure.

The invention claimed is:

1. A method of manufacturing sensor modules, each sensor module having a first housing portion and a second housing portion, the method comprising:
providing a continuous length of at least a first composite sensor fiber;
disposing the first composite sensor fiber across a plurality of first housing portions so that the first housing portions are spaced from each other along the first composite sensor fiber;
coupling a plurality of second housing portions to the first housing portions to form a plurality of sensors modules that are spaced from each other along the first composite sensor fiber, the sensor modules of the plurality being joined together along the continuous length of the first composite sensor fiber; and
separating the sensor modules of the plurality by cutting the first composite sensor fiber into segments without cutting the first and second housing portions.

2. The method claim 1, wherein the segments of the first composite sensor fiber form working electrodes.

3. The method of claim 1, further comprising:
providing a continuous length of a second composite sensor fiber; and
disposing the second composite sensor fiber across the plurality of first housing portions adjacent to the first composite sensor fiber;
wherein separating the sensor modules of the plurality also includes cutting the second composite sensor fiber into segments.

4. The method of claim 3, wherein the segments of the first composite sensor fiber form working electrodes and the segments of the second composite sensor fiber form counter electrodes.

5. The method of claim 1, further comprising assembling the first housing portions including disposing a skin-piercing member at each first housing portion.

6. The method of claim 5, wherein the skin-piercing members are positioned at the first housing portions before the second housing portions are coupled to the first housing portions.

7. The method of claim 5, wherein disposing the first composite sensor fiber across the plurality of first housing portions comprises disposing the first composite sensor fiber parallel to a movement axis of the skin-piercing members.

8. The method of claim 5, wherein disposing the first composite sensor fiber across the plurality of first housing portions comprises disposing the first composite sensor fiber perpendicular to a movement axis of the skin-piercing members.

9. The method of claim 1, wherein disposing the first composite sensor fiber across the plurality of first housing portions comprises disposing the first composite sensor fiber across a length of each first housing portion.

10. The method of claim 1, wherein disposing the first composite sensor fiber across the plurality of first housing portions comprises disposing the first composite sensor fiber across a width of each first housing portion.

11. The method of claim 1, wherein disposing the first composite sensor fiber across the plurality of first housing portions comprises disposing the first composite sensor fiber across a portion of each first housing portion.

12. The method of claim 11, wherein the portion is an analysis cell housing portion.

13. The method of claim 1, further comprising assembling the first housing portions including disposing electrode contacts at each first housing portion, the electrode contacts having contact pads.

14. The method of claim 13, wherein one of the first composite sensor fiber and the electrode contacts is disposed at a location offset from another of the first composite sensor fiber and the electrode contacts.

* * * * *